US012685807B2

(12) United States Patent
Tsoory

(10) Patent No.: US 12,685,807 B2
(45) Date of Patent: Jul. 21, 2026

(54) SYSTEMS, DEVICES AND METHODS FOR PERITONEAL DIALYSATE PRODUCTION AND DELIVERY

(71) Applicant: Liberdi Ltd., Or Akiva (IL)

(72) Inventor: Hezkiah Tsoory, Maor (IL)

(73) Assignee: Liberdi Ltd., Or Akiva (IL)

( * ) Notice: Subject to any disclaimer, the term of this patent is extended or adjusted under 35 U.S.C. 154(b) by 719 days.

(21) Appl. No.: 17/757,668

(22) PCT Filed: Dec. 17, 2020

(86) PCT No.: PCT/IB2020/062117
§ 371 (c)(1),
(2) Date: Jun. 17, 2022

(87) PCT Pub. No.: WO2021/124204
PCT Pub. Date: Jun. 24, 2021

(65) Prior Publication Data
US 2023/0014172 A1 Jan. 19, 2023

(30) Foreign Application Priority Data
Dec. 18, 2019 (WO) .................. PCT/IB2019/060984

(51) Int. Cl.
*A61M 1/28* (2006.01)
*A61M 1/16* (2006.01)
*A61M 1/14* (2006.01)

(52) U.S. Cl.
CPC .......... *A61M 1/287* (2013.01); *A61M 1/1656* (2013.01); *A61M 1/169* (2013.01);
(Continued)

(58) Field of Classification Search
CPC .... A61M 1/159; A61M 1/1656; A61M 1/169; A61M 1/1696; A61M 1/281; A61M 1/287
See application file for complete search history.

(56) References Cited

U.S. PATENT DOCUMENTS

2002/0162778 A1 11/2002 Peabody et al.
2017/0281846 A1 10/2017 Manda et al.
(Continued)

FOREIGN PATENT DOCUMENTS

BR 112018015694 A2 12/2018
BR 112019015744 A2 3/2020
(Continued)

OTHER PUBLICATIONS

International Search Report and Written Opinion of International Searching Authority for PCT/IB2020/062117, ISA/IL, Jerusalem, IsraelDated: Mar. 31, 2021.
(Continued)

*Primary Examiner* — John Kim
(74) *Attorney, Agent, or Firm* — M&B IP Analysts, LLC

(57) ABSTRACT

Embodiments pertain to a peritoneal dialysate production and delivery (PD) system configured to produce fresh dialysate for use in peritoneal dialysis of a patient, the system comprising: a water inlet, a water treatment device that is fluidly connectable or connected via the water inlet to a water source and configured to treat water received from the water source to generate treated water; a concentrate supply device that is in fluid communication with the at least one water treatment device to add concentrate comprised in the concentrate supply device to the treated water to generate fresh dialysate fluid; tubing having a lumen for supplying the fresh dialysate fluid to a patient body via a flow path; and a tubing disinfectant supply device that contains and/or that is operable to receive disinfectant agents, wherein the tubing disinfectant supply device is in fluid connection with the tubing for disinfecting at least a portion of the tubing.

18 Claims, 19 Drawing Sheets

(52) U.S. Cl.
CPC .......... *A61M 1/1696* (2013.01); *A61M 1/281* (2014.02); *A61M 1/159* (2022.05)

(56)     References Cited

U.S. PATENT DOCUMENTS

| | | | |
|---|---|---|---|
| 2017/0281847 A1 | 10/2017 | Manda et al. | |
| 2017/0319769 A1 | 11/2017 | Wieslander et al. | |
| 2017/0340794 A1 | 11/2017 | Hahne et al. | |
| 2018/0021500 A1 | 1/2018 | Gerber et al. | |
| 2019/0125954 A1 | 5/2019 | Mathiot et al. | |
| 2019/0381231 A1 | 12/2019 | Tsoory et al. | |
| 2020/0155744 A1 | 5/2020 | Tsoory et al. | |

FOREIGN PATENT DOCUMENTS

| | | | |
|---|---|---|---|
| CN | 107073250 | A | 8/2017 |
| CN | 108883221 | A | 11/2018 |
| CN | 1088832222 | A | 11/2018 |
| CN | 109589467 | A | 4/2019 |
| CN | 110234371 | A | 9/2019 |
| EP | 1399193 | B1 | 3/2004 |
| EP | 3411093 | A1 | 12/2018 |
| EP | 3576808 | A1 | 12/2019 |
| JP | 2002539896 | A | 11/2002 |
| JP | 2019509149 | A | 4/2019 |
| JP | 2020518302 | A | 6/2020 |
| MX | 2018009298 | A | 1/2019 |
| MX | 2019008791 | A | 9/2019 |
| WO | 02066099 | A2 | 8/2002 |
| WO | 2017134657 | A1 | 8/2017 |
| WO | 2018142406 | A1 | 8/2018 |

OTHER PUBLICATIONS

Chinese Office Action, Chinese Patent Application. CN202080088919. 4, dated Jun. 28, 2025. China National Intellectual Property Administration, Beijing, China.

European Office Action for Patent Application No. EP20901188.1 dated Dec. 12, 2023, 01 page. European Patent Office, Munich, Germany.

Extended European Search Report for European Application No. EP20901188, mailed Nov. 23, 2023, 10 Pages. European Patent Office, Munich, Germany.

Japanese Office Action for Patent Application No. JP2022-537654 dated May 30, 2023, 08 pages. Japan Patent Office, Tokyo, Japan.

Mexican Office Action for Patent Application No. MX/a/2022/007673 dated Jun. 16, 2025, 08 pages. Mexican Institute of Industrial Property, Mexico City, Mexico.

Brazilian Search Report for Patent Application No. BR1120220117566 dated Nov. 10, 2025, 08 pages.

European Office Action for Patent Application No. EP20901188.1 dated Nov. 24, 2025, 07 page.

Indian Office Action for Patent Application No. IN202247040857 dated Dec. 5, 2025, 06 pages.

Mexican Office Action for Patent Application No. MX/a/2022/007673 dated Sep. 18, 2025, 05 pages.

Second Office Action for CN application No. 202080088919.4, dated Apr. 13, 2026. China National Intellectual Property Administration, Beijing, China.

Peritoneal Dialysate Production and Delivery System 1000A

FIG. 1

Peritoneal Dialysate Production and Delivery System 1000A

Tubing Disinfection Stage

FIG. 3

Peritoneal Dialysate Production and Delivery System 1000A

Fresh Dialysate Delivery Stage

FIG. 4

Peritoneal Dialysate Production and Delivery System 1000A

Used Dialysate Drain Stage

FIG. 5

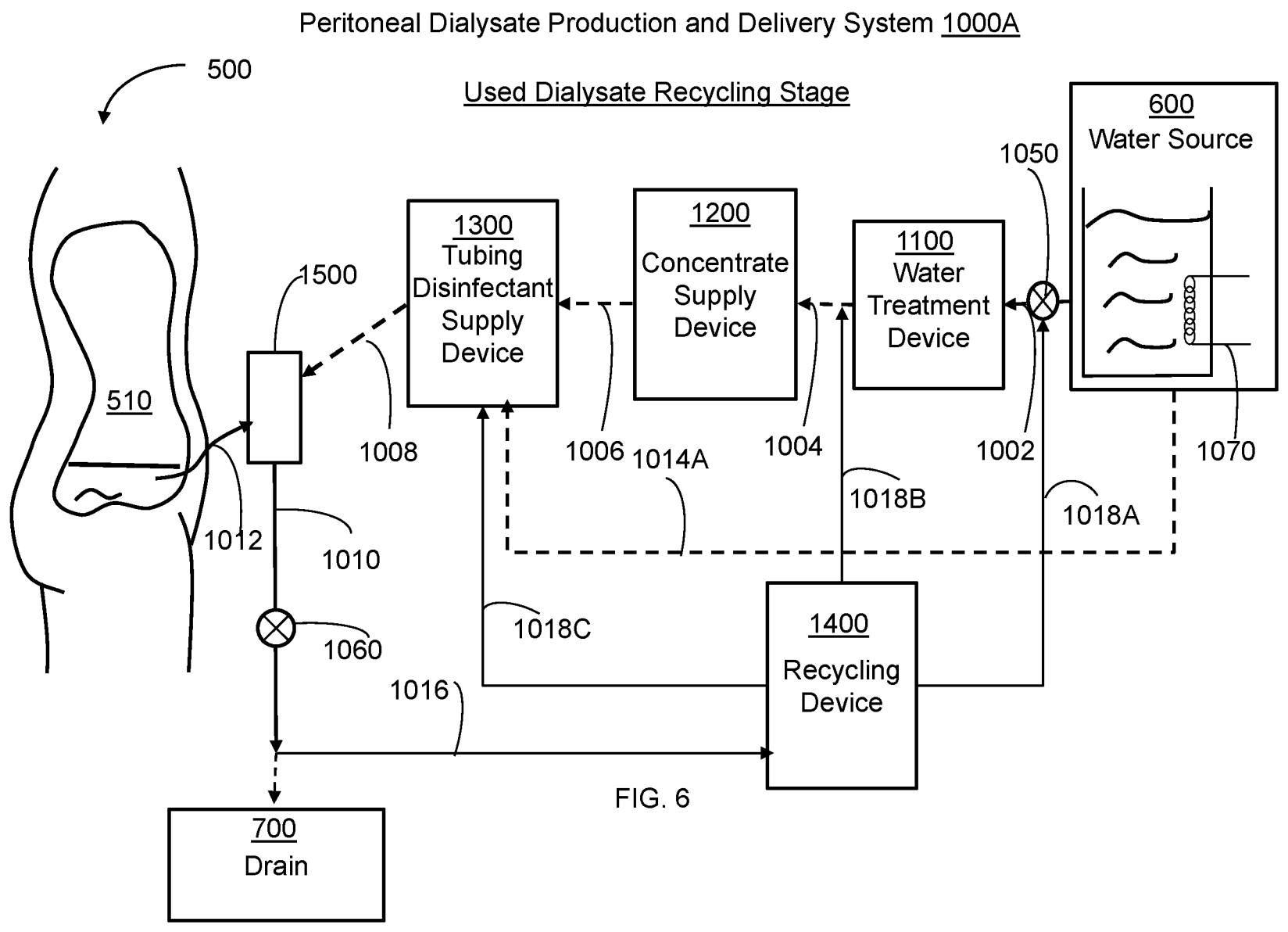

Peritoneal Dialysate Production and Delivery System 1000A

Used Dialysate Recycling Stage

600 Water Source

1070

1050

1002

1018A

1100 Water Treatment Device

1018B

1400 Recycling Device

1004

1200 Concentrate Supply Device 1006 1014A

1018C

1300 Tubing Disinfectant Supply Device

1008

1500

510

500

1012

1010

1060

1016

700 Drain

FIG. 6

Figure 8:
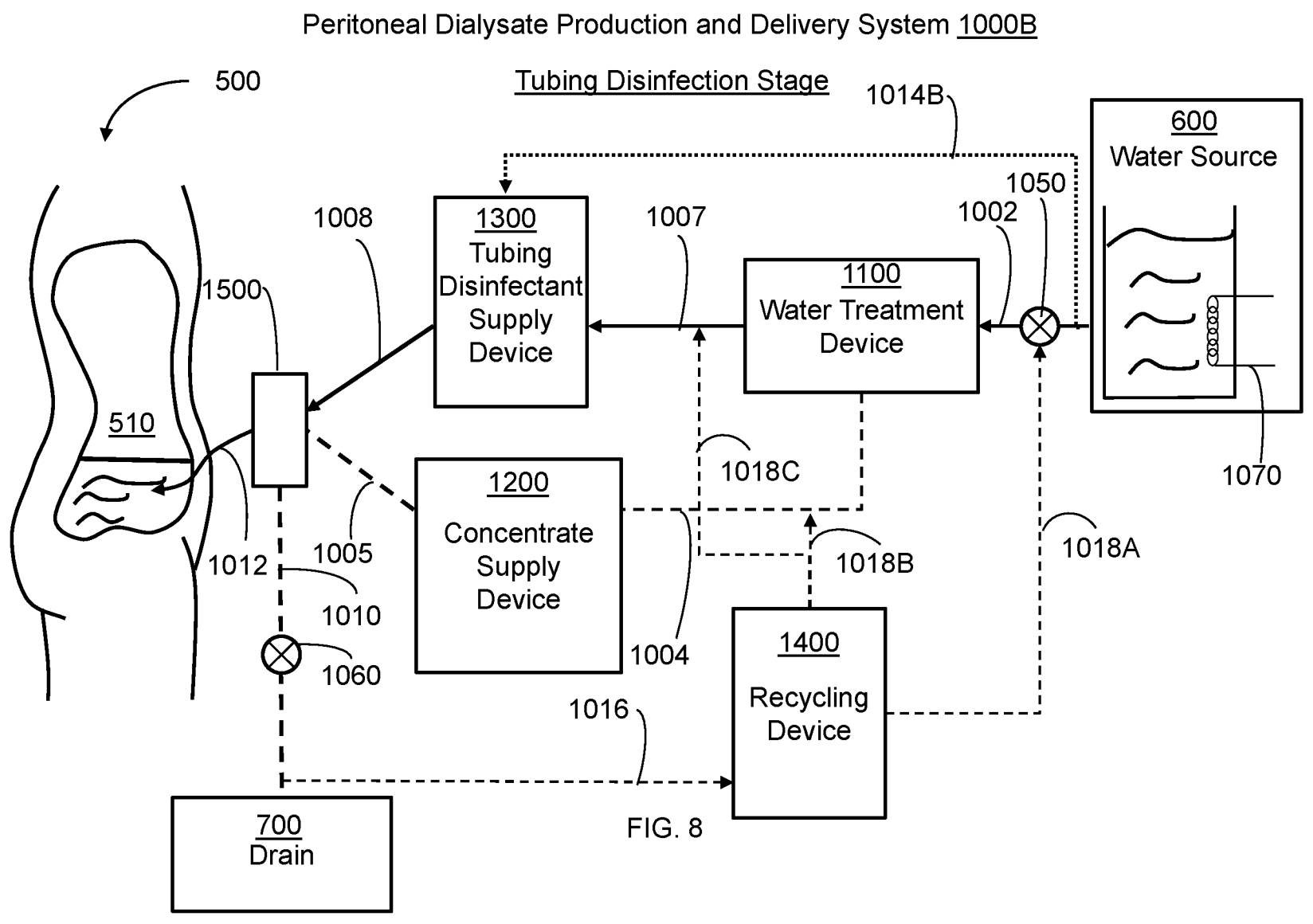

Peritoneal Dialysate Production and Delivery System 1000B

Tubing Disinfection Stage 1014B

600 Water Source

1070

1050

1002

1018A

1100 Water Treatment Device

1014B

1018B

1400 Recycling Device

1018C

1007

1004

1300 Tubing Disinfectant Supply Device

1200 Concentrate Supply Device

1008

1005

1010

1060

1500

1012

500

510

700 Drain

Figure 9:
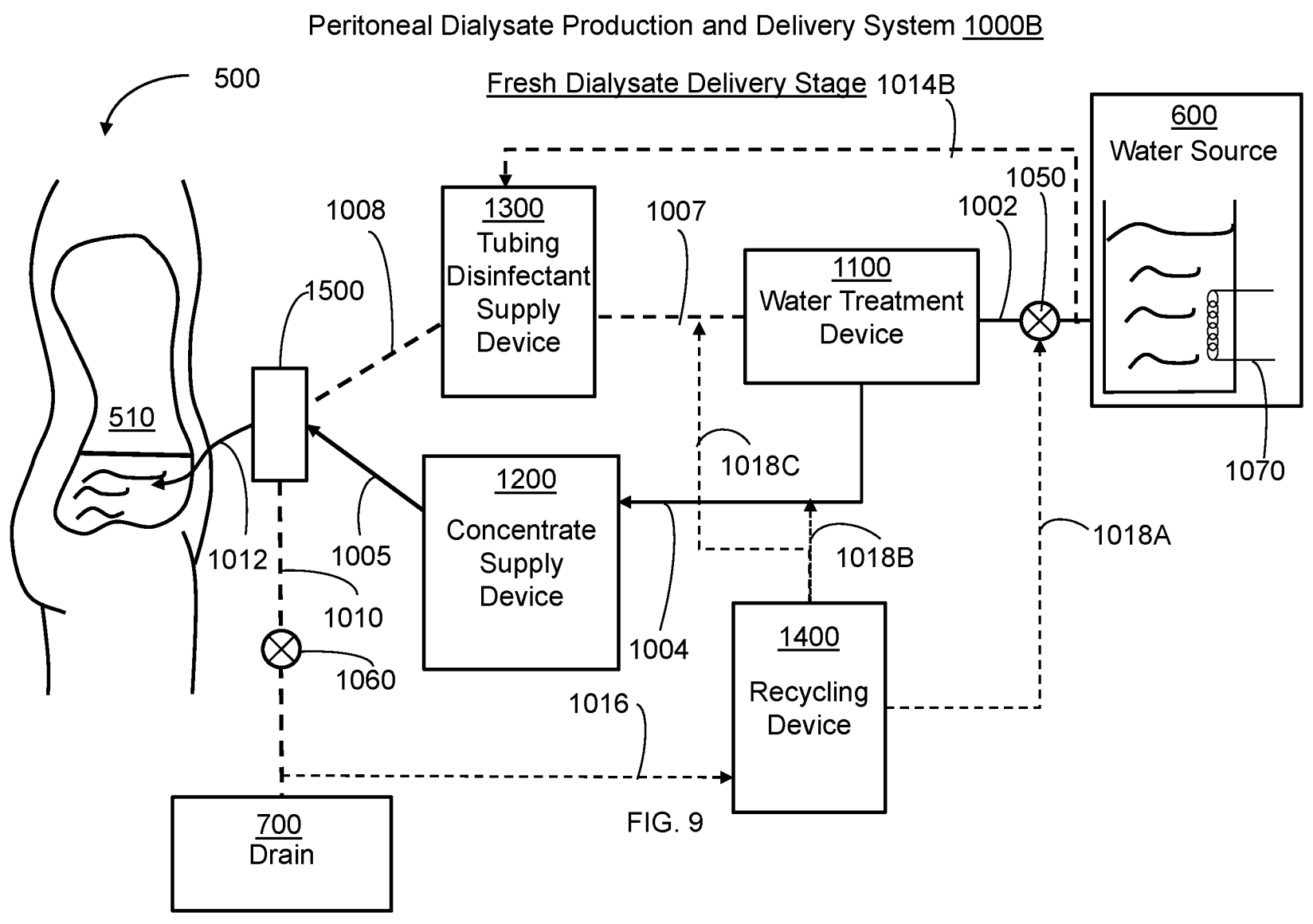

Peritoneal Dialysate Production and Delivery System 1000B

Fresh Dialysate Delivery Stage 1014B

600 Water Source

1070

1050

1002

1018A

1100 Water Treatment Device

1018B

1400 Recycling Device

1018C

1007

1004

1300 Tubing Disinfectant Supply Device

1200 Concentrate Supply Device

1008

1500

1005

1010

1060

1012

500

510

700 Drain

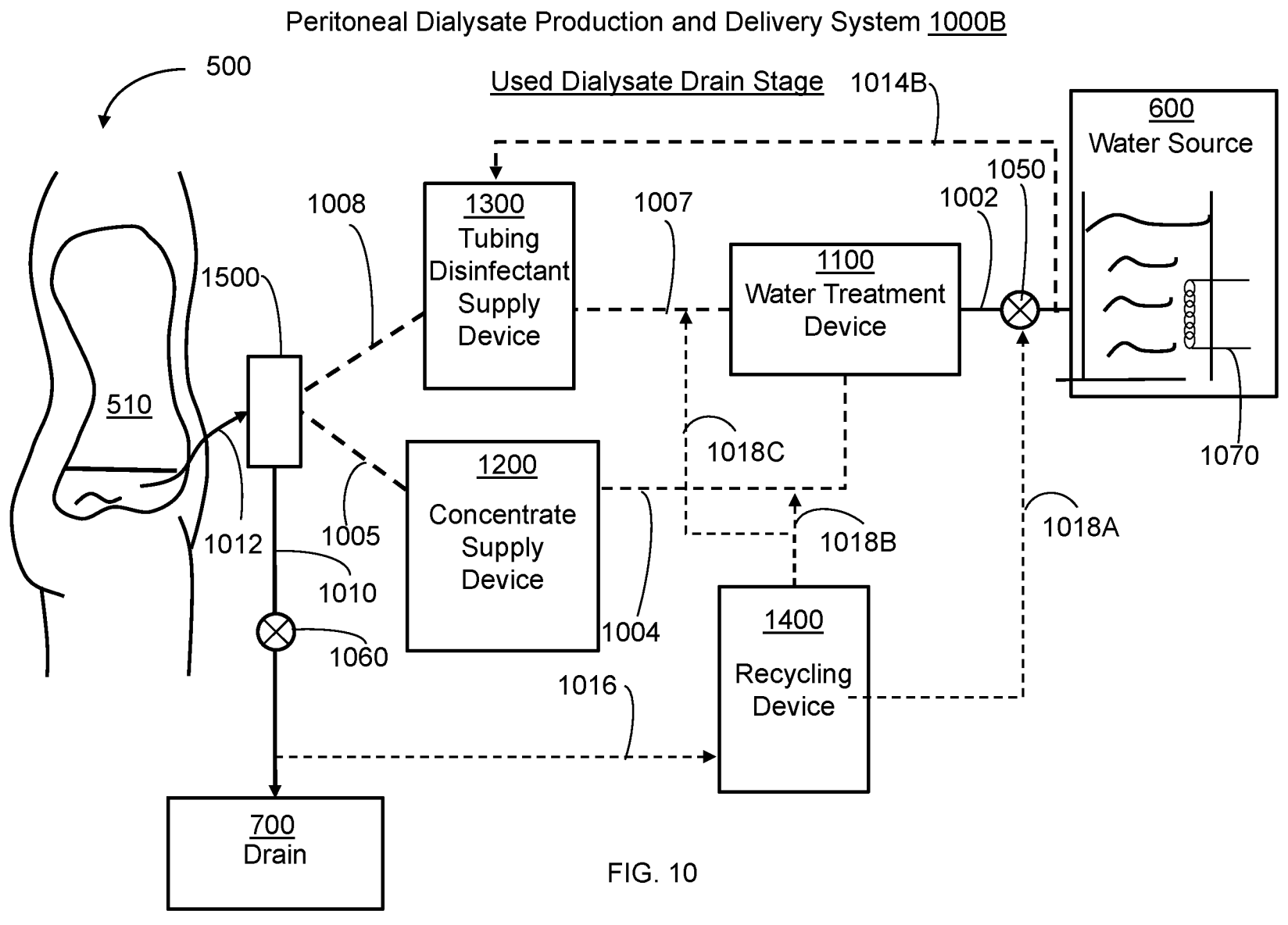

Peritoneal Dialysate Production and Delivery System 1000B

Used Dialysate Drain Stage　1014B

600 Water Source

1070

1050

1002

1100 Water Treatment Device

1018A

1018B

1018C

1400 Recycling Device

1007

1300 Tubing Disinfectant Supply Device

1200 Concentrate Supply Device

1004

1008

1005

1010

1016

1060

500

510

1500

1012

700 Drain

FIG. 10

Figure 11:
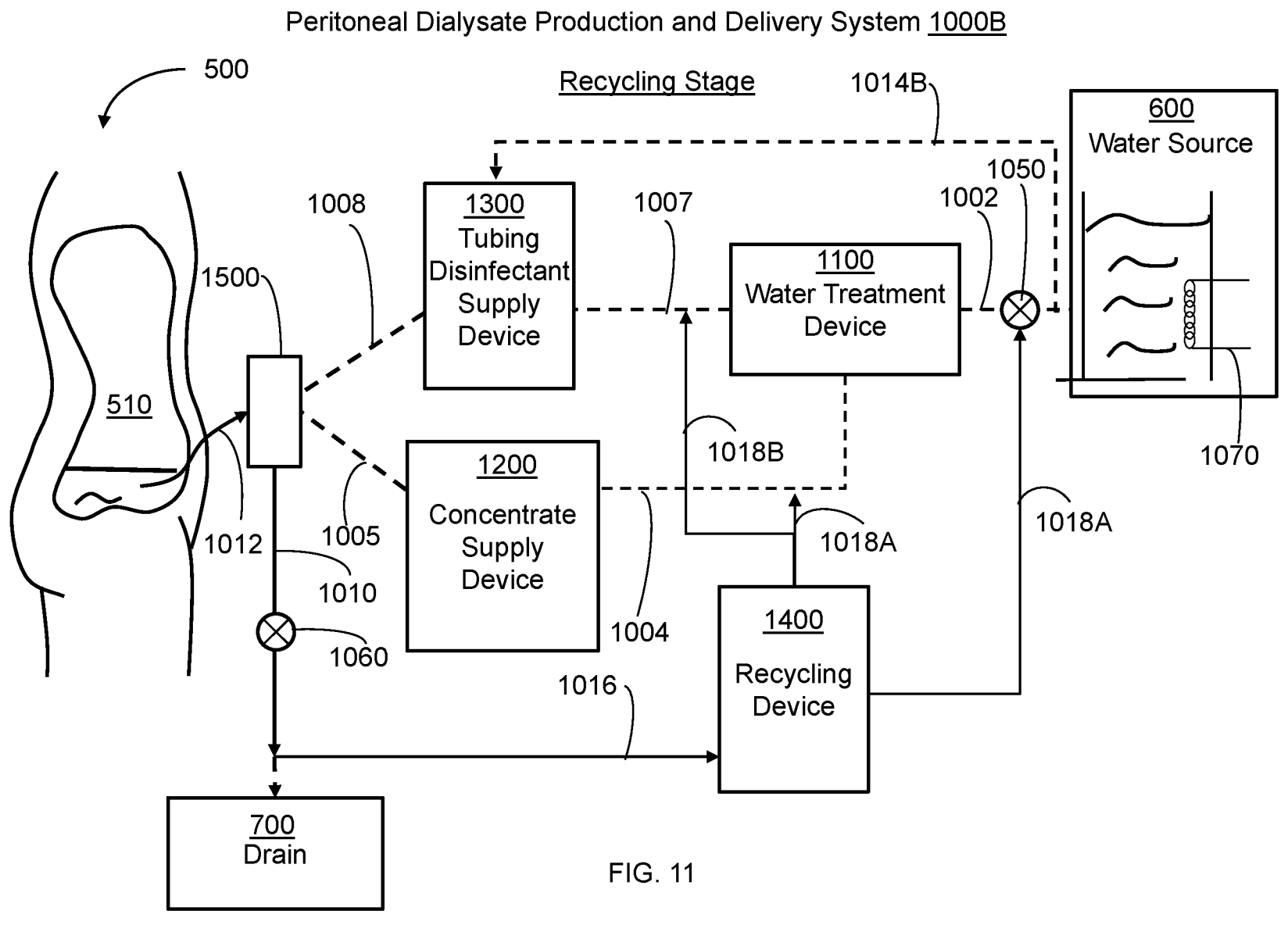

Peritoneal Dialysate Production and Delivery System 1000B

Recycling Stage

600 Water Source

1070

1050

1002

1100 Water Treatment Device

1018A

1018A

1014B

1018B

1400 Recycling Device

1007

1004

1016

1300 Tubing Disinfectant Supply Device

1200 Concentrate Supply Device

1008

1005

1010

1060

1500

510

1012

500

700 Drain

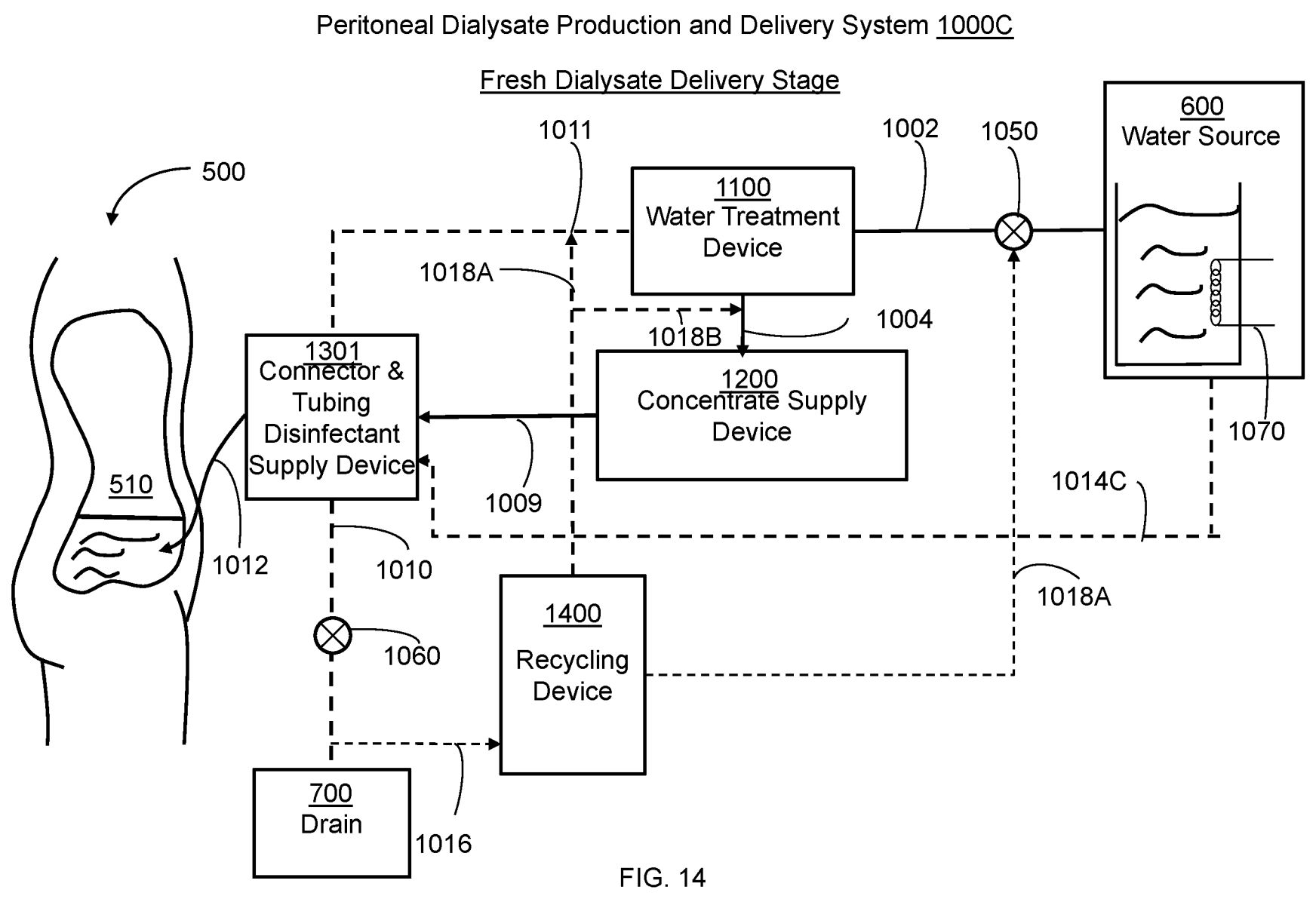

Peritoneal Dialysate Production and Delivery System 1000C

Fresh Dialysate Delivery Stage

FIG. 14

600 Water Source

1070

1014C

1018A

1050

1002

1004

1100 Water Treatment Device

1200 Concentrate Supply Device

1018B

1011

1018A

1009

1400 Recycling Device

1301 Connector & Tubing Disinfectant Supply Device

1010

1060

700 Drain

1016

500

510

1012

Peritoneal Dialysate Production and Delivery System 1000C

Used Dialysate Drain Stage

FIG. 15

Figure 16:
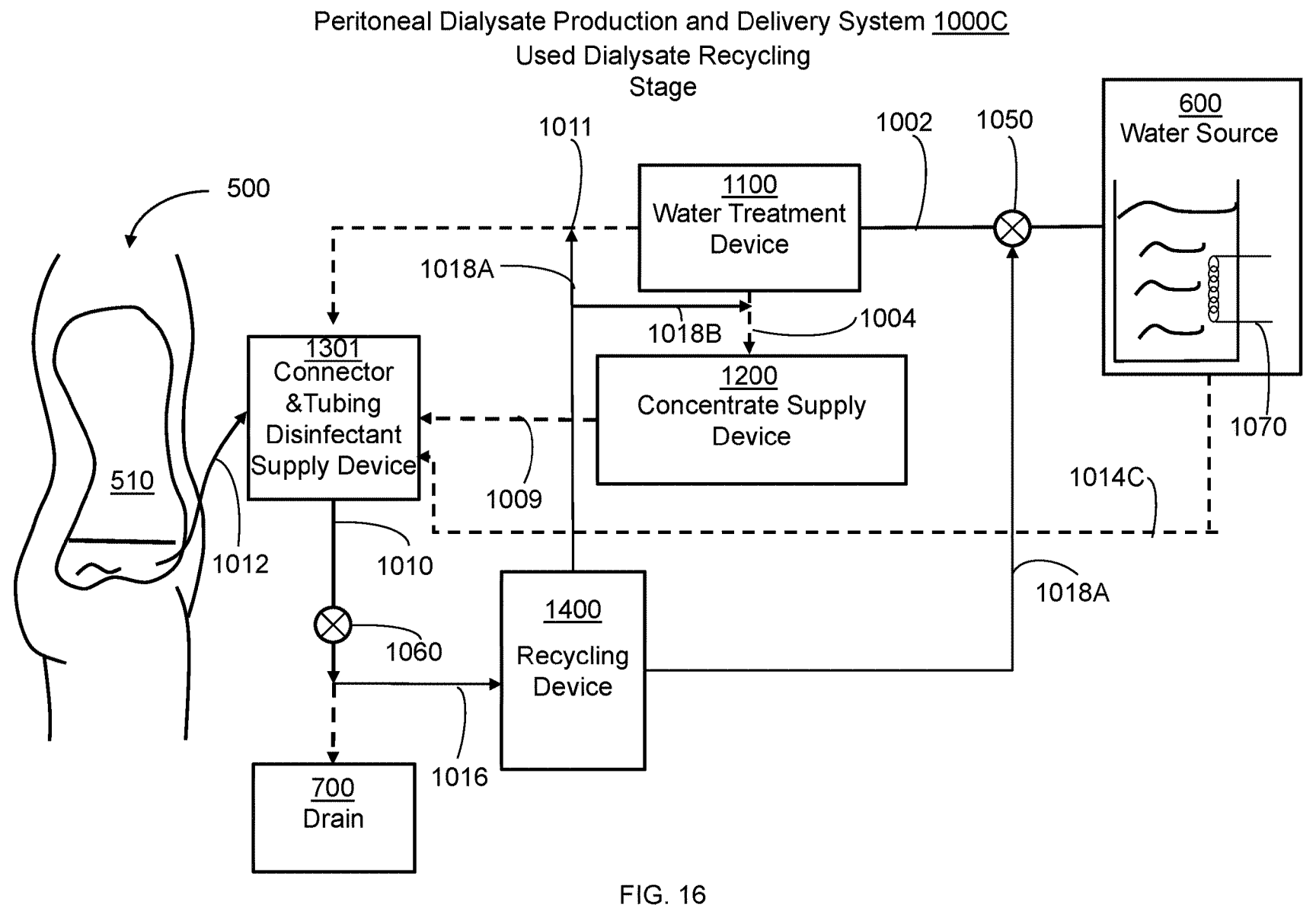

Peritoneal Dialysate Production and Delivery System 1000C
Used Dialysate Recycling Stage 600 Water Source

1070

1050

1002

1014C

1018A

1100 Water Treatment Device

1004

1018B

1200 Concentrate Supply Device

1011

1018A

1009

1400 Recycling Device

1301 Connector & Tubing Disinfectant Supply Device

1010

1060

1016

700 Drain

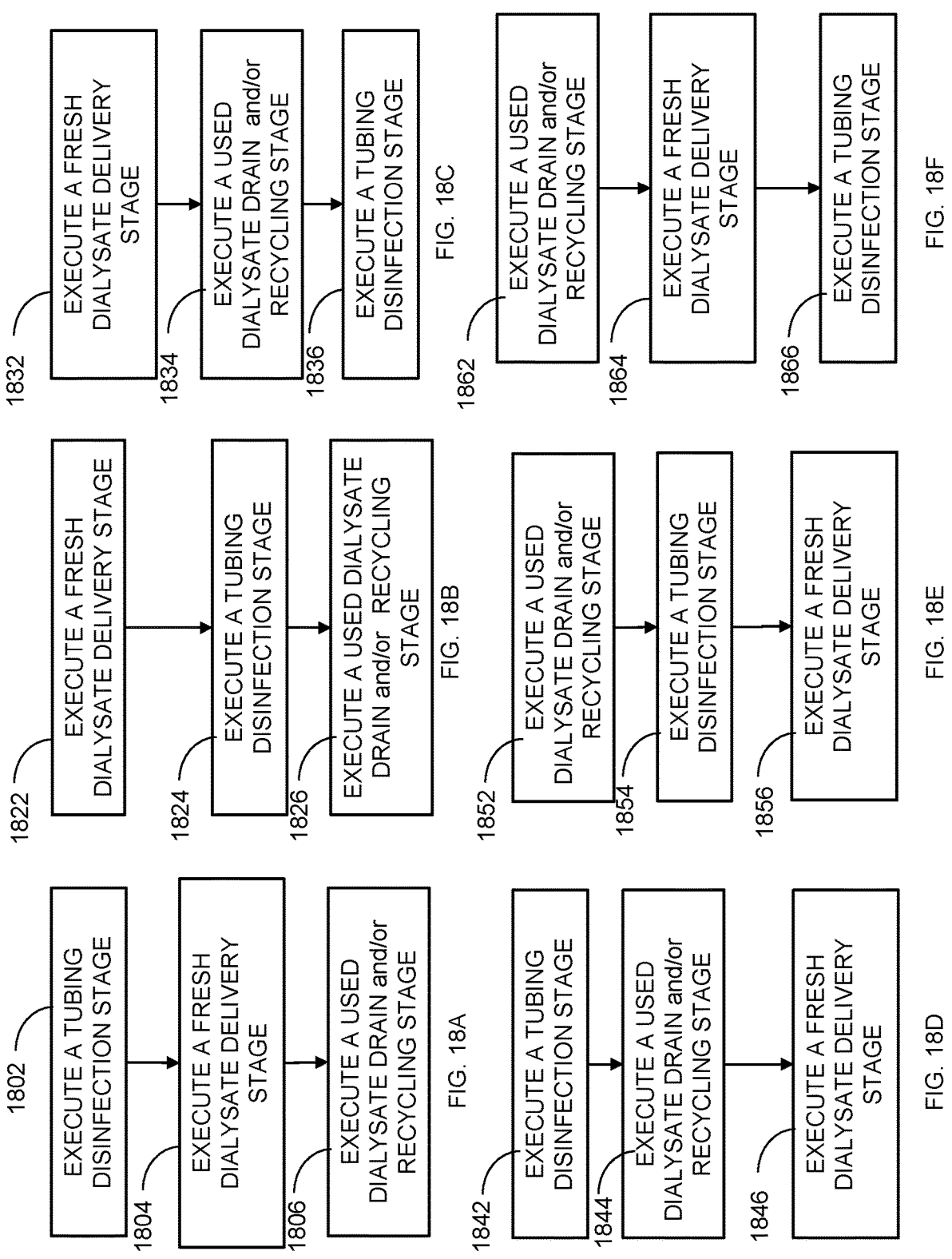

1832 — EXECUTE A FRESH DIALYSATE DELIVERY STAGE

1834 — EXECUTE A USED DIALYSATE DRAIN and/or RECYCLING STAGE

1836 — EXECUTE A TUBING DISINFECTION STAGE

FIG. 18C

1862 — EXECUTE A USED DIALYSATE DRAIN and/or RECYCLING STAGE

1864 — EXECUTE A FRESH DIALYSATE DELIVERY STAGE

1866 — EXECUTE A TUBING DISINFECTION STAGE

FIG. 18F

1822 — EXECUTE A FRESH DIALYSATE DELIVERY STAGE

1824 — EXECUTE A TUBING DISINFECTION STAGE

1826 — EXECUTE A USED DIALYSATE DRAIN and/or RECYCLING STAGE

FIG. 18B

1852 — EXECUTE A USED DIALYSATE DRAIN STAGE

1854 — EXECUTE A TUBING DISINFECTION STAGE

1856 — EXECUTE A FRESH DIALYSATE DELIVERY STAGE

FIG. 18E

1802 — EXECUTE A TUBING DISINFECTION STAGE

1804 — EXECUTE A FRESH DIALYSATE DELIVERY STAGE

1806 — EXECUTE A USED DIALYSATE DRAIN and/or RECYCLING STAGE

FIG. 18A

1842 — EXECUTE A TUBING DISINFECTION STAGE

1844 — EXECUTE A USED DIALYSATE DRAIN and/or RECYCLING STAGE

1846 — EXECUTE A FRESH DIALYSATE DELIVERY STAGE

FIG. 18D

SYSTEMS, DEVICES AND METHODS FOR PERITONEAL DIALYSATE PRODUCTION AND DELIVERY

TECHNICAL FIELD

Aspects of the present disclosure relate in general to dialysis systems, methods and devices including, for example, to peritoneal dialysis.

BACKGROUND

Peritoneal and hemodialysis have been in use for many years. While hemodialysis uses an artificial membrane to remove toxins and excess water from the blood of a renal patient, peritoneal dialysis uses the natural peritoneal membrane of the patient's peritoneum (also: abdominal cavity).

In peritoneal dialysis, a peritoneal solution (also: dialysis or dialysate fluid) is infused into the patient's peritoneal cavity via the abdominal wall. The dialysate remains in the peritoneal cavity for a dwell period to allow waste, toxins and excess water to pass across the peritoneal membrane (also known as ultrafiltration), due to osmosis and/or diffusion, from the patient's bloodstream into the dialysate. Used dialysate is then drained from the patient to remove, along with the dialysate, waste, toxins and excess water from the patient. The description above is presented as a general overview of related art in this field and should not be construed as an admission that any of the information it contains constitutes prior art against the present patent application.

BRIEF DESCRIPTION OF THE FIGURES

The figures illustrate generally, by way of example, but not by way of limitation, various embodiments discussed in the present document. For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. References to previously presented elements are implied without necessarily further citing the drawing or description in which they appear. The figures are listed below.

FIG. 1 is a schematic illustration of a peritoneal dialysate production and delivery system, according to some embodiments.

FIG. 3 is a schematic illustration of a tubing disinfection stage, according to some embodiments.

FIG. 4 is a schematic illustration of a fresh dialysate delivery stage, according to some embodiments.

FIG. 5 is a schematic illustration of a used dialysate drain stage, according to some embodiments.

FIG. 6 is a schematic illustration of a used dialysate recycling stage, according to some embodiments.

FIG. 8 is a schematic illustration of a tubing disinfection stage, according to some other embodiments.

FIG. 9 is a schematic illustration of a fresh dialysate delivery stage, according to some other embodiments.

FIG. 10 is a schematic illustration of a used dialysate drain stage, according to some other embodiments.

FIG. 11 is a schematic illustration of a used dialysate recycling stage, according to some other embodiments.

FIG. 13 is a schematic illustration of a tubing disinfection stage, according to some alternative embodiments.

FIG. 14 is a schematic illustration of a fresh dialysate delivery stage, according to some alternative embodiments.

FIG. 15 is a schematic illustration of a used dialysate drain stage, according to some alternative embodiments.

FIG. 16 is a schematic illustration of a used dialysate recycling stage, according to some alternative embodiments.

FIGS. 18A-F are method flow charts of various stage sequences for performing a disinfection stage, a fresh dialysate delivery stage, and a used dialysate drain stage.

DETAILED DESCRIPTION

Figure 2:
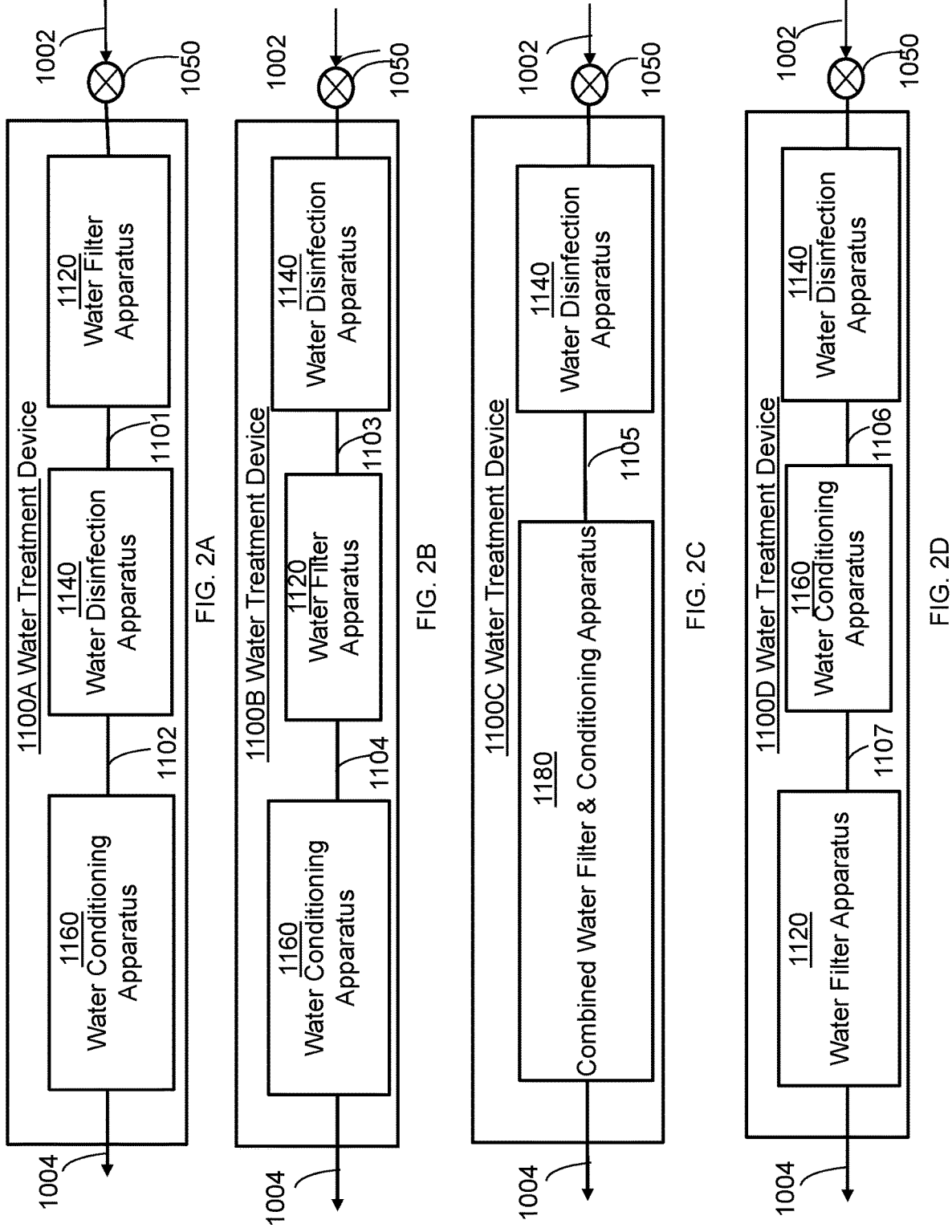
FIGS. 2A-D are schematic illustrations of various water treatment device configurations, according to some embodiments.

The following description of peritoneal dialysate production and delivery (PD) systems and related devices and methods for producing dialysate for use by a patient in a peritoneal dialysis cycle is given with reference to particular examples, with the understanding that such systems, devices and methods are not limited to these examples.

Aspects of embodiments pertain to PD systems that are man-portable (also: mobile), easy-to-use and employable in a variety of ambulatory or outpatient care settings such as in a domestic environment and/or while the patient is traveling (e.g., by airplane, train). Optionally, the PD system may be configured to produce dialysate to an amount that suffices for a plurality of dialysis cycles, for two peritoneal dialysis cycles or less, or for a single peritoneal dialysis cycle, or less. Optionally, the PD system may be configured as a cartridge. Optionally, the PD system may be configured to provide fresh dialysate that suffices for a single exchange, batch or peritoneal dialysis cycle.

In some embodiments, the PD system's fresh dialysate production capacity may be in the range of, for example, 1-3 liters, 1 to 15 liters, or 6 to 15 liters.

In some embodiments, the PD System may be operable to produce a predetermined amount of fresh dialysate fluid. For example, a kit may comprise a plurality of PD systems, each PD system of the kit being operable to produce a predetermined amount of fresh dialysate fluid.

In some other embodiments, the PD system may be operable to provide a variable amount of fresh dialysate fluid, e.g., depending on the patient needs.

In some embodiments, the PD system may be configured to bridge a time gap during which a cycler system capable of performing multiple cycles may not be readily available to the patient for use.

Optionally, at least some or all components of the PD system may be configured for single-use (e.g., disposable). Optionally, at least some or all components of the PD system may be configured as a cartridge. Optionally, PD system may comprise a housing (e.g., of an exchangeable cartridge configuration) enclosing some or all PD system components.

At least some or all components of the PD system may be configured for single-use. At least some or all components of the PD system may be disposable. Optionally, tubing or any other surfaces of equipment of the PD system that can engage with water during regular use may be made of polymer-based material.

In some embodiments, the PD system may be configured to be entirely mechanically operable, i.e., without requiring any electrical power supply such as a battery and/or connection to an electrical grid. Optionally, the PD system may be exclusively mechanically yet nevertheless at least partially automatically operable. Optionally, the PD system may be semi-automatically operable, with or without requiring electrical power supply.

In some embodiments, the PD system may require electrical power supply such as a battery, to allow for automated sensing functionalities of system operating parameters and related controls, as will be outlined herein in more detail.

A water pressurizing device such as a supply pump may be employed for expending energy onto water to force water received from the water source through the PD system for providing the patient with fresh dialysate fluid. Optionally, the supply pump may be separate from the PD system and employable for a plurality of PD systems. Optionally, the supply pump may be comprised in the PD system.

In some embodiments, a water pressure regulation apparatus may be employed to ensure that the water pressure entering the patient's peritoneal cavity meets a patient supply pressure criterion. Optionally, the patient supply pressure criterion may define an upper threshold or limit of, for example, 0.08 bar (combined static and dynamic water pressure).

In some embodiments, the PD system may include one or more water treatment devices which are configured to process source feed water received by the water treatment device to provide treated water suitable for the generation of a dialysate solution (also: fresh dialysate fluid). A water treatment device may receive water from, for example, a source of potable water (also: water intended for human consumption) such as a residential water source or any other source feed water that is not necessarily covered, for example, by a pharmacopoeial monograph. The term "treated water" as used herein can pertain to Purified Water, Water for Injection (WFI) (e.g., as defined by US or European Pharmcopeia) and/or any water of higher quality than potable water.

In some embodiments, the water treatment device may be operable to generate treated water that is suitable to receive additives for generating dialysate fluid and may be include, for example, a water filter, a water disinfection apparatus, and/or a water conditioning apparatus.

In some embodiments, the PD system may comprise a water quality sensor operative to sense a physical quantity or characteristic indicative of water quality and provide an output responsive to the sensed physical quantity and/or characteristic. Optionally, water quality of fresh dialysate and/or of used dialysate may be measured by the water quality sensor. It is noted that the expressions "used dialysate", "used dialysate fluid", "used dialysis fluid", "used peritoneal dialysate" and "effluent", may herein be used interchangeably.

Optionally, based on the sensed physical quantity/characteristic indicative of water quality, an operational status of the PD system may be determined. For example, based on the sensed physical quantity it may be determined, for example, whether it is necessary to discard the presently used PD system and replace it with an unused PD system.

Aspects of embodiments may pertain to a kit comprising a plurality of PD systems (also: PD cartridge systems) that are operable and employable according to recommended or prescribed treatment regimens (e.g., predetermined fresh dialysate volume, filtration regimen, medication regimen, and/or the like). Optionally, at least two of the plurality of PD systems of a kit may have different operating parameters and/or configurations.

A PD system of the plurality of PD systems can be selected in accordance with a clinical condition of a patient. Optionally, a kit may be employed to treat different patients in accordance with their clinical condition. Optionally, a kit may be employed to treat the same patient in accordance with the patient's (optionally varying) clinical condition.

Optionally, a presently used PD system (e.g., of a kit) by a patient may provide an output indicative of a recommendation (e.g., recommended prescription) regarding the operating characteristics of a PD system (e.g., of a kit) to be subsequently employed by the same patient. Optionally, operating characteristic of a PD may for example pertain to medication agents, ultrafiltration agents, solutes, volume of fresh dialysate, and/or the like.

For example, the presently used PD system which may produce fresh dialysate without a medication agent admixed to it, may provide an output indicative of a recommendation that the PD system for subsequent use by the patient shall produce a fresh dialysate with a medication agent admixed to it such as, for example, antibiotics.

In some embodiments, based on an output provided by each one of a plurality of PD systems that were used by the same or a plurality of different patients, a treatment recommendation/prescription may be provided for a desired patient.

In some embodiments, a sensing apparatus may be employed by the PD system(s) for providing the output relating to a required patient treatment regimen. The sensing apparatus may comprise a water quality sensor, an infection level sensor (e.g., turbidity sensor), flow rate sensor, dialysate waste products sensor (e.g., urea level, creatinine level sensor), and/or the like.

Optionally, the same sensing apparatus may be employed for a plurality of PD systems. Optionally, each PD system may comprise a sensing apparatus for providing an output indicative of a required patient treatment regimen.

In some embodiments, sensing apparatus may comprise an infection level sensor, e.g., for self-calibration of the PD system presently in use. Self-calibration may for example be performed based on drained dialysate, e.g., as described in International Patent Application WO2018142406 filed on 1 Feb. 2018 and which is incorporated herein by reference in its entirety.

The water treatment device may be fluidly connected or connectable, via a feed water inlet of the water treatment device, with a source feed water supply. Processing (also: treating) water to arrive at treated water can include, for example, water filtration, water conditioning, water purification (e.g., disinfecting) and/or the like.

A decoupling output may be provided by the PD system to indicate if sufficient potable water was supplied to the water treatment device. If sufficient potable water was supplied, the PD system can be fluidly decoupled from the feed water source. In some embodiments, the fluid decoupling of the PD system from the feed water source may be controlled automatically, responsive to the decoupling output signal that may be provided by a corresponding sensor (e.g., a water level sensor).

In some embodiments, the PD system may comprise a concentrate supply device that is in fluid communication with the water treatment device to receive treated water from the water treatment device, via a corresponding flow path. The concentrate supply device is configured to add concentrate to the treated water to generate fresh dialysate fluid from the treated water. Concentrate added to the treated water in the concentrate supply device is, for example, suitable to generate an osmotic gradient required for conducting peritoneal dialysis. In embodiments, the concentrate can include an osmotic agent such as, for example, monosaccharides (e.g., glucose, dextrose), polysaccharide, polyamides and/or polypeptides. Optionally, additional agents (e.g., substances, composition and/or compounds) may be added to the water such as, for example, buffer solutions (e.g., CH3CH(OH)COO, also known as lactic acid) to maintain the water pH values within a desired range, and/or electrolytes (e.g., sodium, potassium, calcium, magnesium and phosphate).

Optionally, the PD system may be operable to controllably and adaptively supply agents in accordance with a sensed parameter such as concentration.

Optionally, the PD system may be operable to produce a preset amount of fresh dialysate having predetermined characteristics.

The terms "in fluid communication", "fluidly coupled", "fluidly coupled" as well as grammatical variations thereof, may herein be used interchangeably.

In some embodiments, the PD system may further comprise tubing having a lumen that is defined by an inner wall and which extends along the tubing's longitudinal axis.

In some embodiments, the PD system may additionally comprise a tubing disinfectant supply device. The tubing disinfectant supply device may contain disinfectant agents and/or may be operable to receive tubing disinfectant agents, e.g., provided by the patient or the medical professional. The disinfecting agent may have disinfecting, sanitizing, sterilizing and/or other decontaminating effects on, for example, metal and/or polymer-based surfaces (e.g., tubing surfaces).

Merely to simplify the discussion that follows, without be construed as limiting, examples disclosed may pertain to the action of disinfecting and the use of the disinfectant agent. However, the term "disinfecting" as used herein may also encompass "sterilizing and/or sanitizing".

In some examples, the expression "disinfectant agent" excludes use of hot fluid as disinfectant agents, such as heated water or steam. In examples, where hot fluid may be employed, piping and instrumentation are made of suitable material such to withstand heat-based disinfection.

In some examples, dextrose may be employed as an osmotic agent. However, in some examples, dextrose is excluded from being used as a disinfectant agent, and a substance or compound different than dextrose may be employed for disinfecting purposes.

In some embodiments, the peritoneal dialysate production and delivery system may be configured to process drained fluid comprising the disinfectant agent and/or disinfection byproducts thereof to obtain fresh dialysate.

Optionally, the tubing disinfectant agent may allow for disinfecting at least some or all the tubing's inner wall. The tubing disinfecting agent may be in the form of, for example, powder; liquid, and/or gel, and may be coated on to the walls of the tubing disinfectant supply device. Optionally, the tubing disinfectant agent may comprise or be gas such as, for example, NOx and/or Ozone. In some embodiments, the disinfecting agent may be released from a disinfecting agent receptacle comprised in the PD system.

In some embodiments, the tubing may comprise a tubing connector and a patient catheter, as will be outlined below in greater detail. Optionally, elements and/or surfaces of parts which are engaging with each other for fluidly coupling the patient catheter with the tubing connector, may be designed such that the disinfectant agent engages with these elements and/or surfaces. For example, during a disinfection stage, connector elements and/or surfaces of the patient catheter and the tubing connector may therefore be operably subjected to disinfectant agent for allowing disinfection of these elements and/or surfaces. In some embodiments, a disinfection agent may be provided or released, for example, as disclosed in International Patent Application WO2017/134657, filed in the name o Liberdi Ltd on 1 Feb. 2017, and which is incorporated herein by reference in its entirety.

In some embodiments, the tubing may comprise various tubing portions or sections, e.g., as outlined herein.

Fresh dialysate fluid may be supplied from the concentrate supply device to the patient's peritoneal cavity via the lumen of fresh dialysate supply tubing defining a fresh dialysate supply flow path.

Used dialysate fluid may be drained from the patient's peritoneal cavity to drain or waste via the lumen of used dialysate waste tubing defining a used dialysate flow path, e.g., through gravity.

In some embodiments, the PD system may be configured to function as a self-sufficient PD system. For example, the PD system may be configured to self-sufficiently perform a plurality of fresh dialysate production cycles by employing a used dialysate water recycling (e.g., recovering) process and by storing in the PD system enough softeners, concentrate (e.g., osmotic agents), tubing disinfectant and/or other agents. The PD system may be configured such that the consumption of agents stored in the PD system during the employment of a fresh-dialysate production cycle allows the self-sufficient production of fresh-dialysate several times. In some embodiments, used dialysate can be recycled, for example, at least 2, 3, 5, 8, 10, 15, 20, or 100 times, to produce fresh dialysate, until the agents and/or equipment used by recycling device must be replaced or refreshed.

In some examples, at least some or all the used dialysate fluid may not be drained but subjected to a recycling stage by delivering (e.g., pumping) at least some, or all or substantially all of the used dialysate fluid towards a recycling device that is configured to remove dialysate waste products from the used dialysate fluid for the purpose of producing recycled feed water. The recycled feed water may be stored in recycling device for later (e.g., on-demand) usage, e.g., to produce fresh dialysate.

In the recycling stage, dialysate waste products may be removed partially, entirely, or substantially entirely from the used dialysate fluid. Dialysate waste products drawn from the patient's blood such as, potassium, phosphate, and other uremic toxins (e.g., urea, creatinine, fibrin and/or other middle weight molecules), may be removed from the fluid by the recycling device to generate recycled feed water.

The recycled feed water may be recirculated for further processing, which may include water conditioning and/or the addition of buffer agents and/or osmotic agents. The employment of the recycling device may render the PD system, at least for a certain number of treatment cycles, entirely self-sufficient. For example, the PD System may be configured to self-sufficiently perform, for example, 2 to 20 (e.g., peritoneal) dialysis treatment cycles. In some examples, the PD System may be configured to self-sufficiently perform, for example, at least 2 to 20 (e.g., peritoneal) dialysis treatment cycles.

In some examples, the recycled feed water may be further processed, e.g., by the one or more apparatuses of the water treatment device. After treatment of the recycled feed water by the one or more apparatuses of the water treatment device, concentrate may be admixed to generate fresh dialysate water.

In some other examples, fresh dialysate fluid may be generated by adding concentrate to the recycled feed water without prior treatment of the recycled feed water by the one or more apparatuses of the water treatment device.

Adding or providing (e.g., admixing) concentrate to recycled feed water may be necessary as the effluent quantity may be larger than the quantity of the fresh dialysate fluid provided.

In some embodiments, the PD system may comprise a drain pump suitable for imparting energy onto used dialysate fluid for drainage thereof from the peritoneal cavity via waste tubing to drain. Optionally, drain pump may be an automatically operable pump, a semi-automatically operable pump and/or a manually operable pump. For instance, drain pump may be a hand-operable air pump implemented by, for example, an expandable and inflatable bag air or bag water pump. In some embodiments, the drain may be a receptacle. Optionally, the drain may be part of the PD system.

In some embodiments, the disinfectant agent may be supplied for disinfecting at least a portion of the inner side wall of the tubing. For example, the disinfecting agent may be supplied for disinfecting a disinfectant supply flow path.

In some embodiments, the tubing disinfecting agent may be delivered to the patient's peritoneal cavity, for instance, for the purpose of disinfecting a patient catheter. Optionally, a portion of the patient catheter may be disposable. Optionally, the amount of tubing disinfecting agents that is delivered to the patient's peritoneal cavity may be controlled, for example, by a sensor.

In some embodiments, the tubing disinfecting agent may be delivered directly to drain. In some embodiments, the tubing disinfecting agent may be used for disinfecting the patient catheter by delivering the agent via the patient catheter to the peritoneal cavity. The disinfecting agent may then be drained from the peritoneal cavity.

In some embodiments, a tubing disinfectant agent purging, or drainage stage may be employed. Such tubing disinfectant agent purging stage may for instance be employed prior to generating and delivering fresh dialysate fluid to the patient's peritoneal cavity.

In some embodiments, the fresh dialysate supply tubing may be part of the fresh dialysate tubing. In some embodiments, the fresh dialysate supply tubing may constitute the fresh dialysate tubing, and vice versa.

The tubing may comprise a patient catheter having a proximal end that can be positioned inside the patient body, and a distal end that is positioned outside the patient body. The term "proximal" as used herein refers to a location which is closer to the patient compared to a "distal" location.

In some embodiments, the fresh dialysate supply tubing may comprise or constitute the patient catheter. The patient catheter may comprise a catheter port and an external catheter portion which is external to the patient body and that may be removably coupleable with the catheter port. The catheter port may be configured for long-term or permanent operable coupling with the patient to provide a passageway from outside the patient body to the patient's peritoneal cavity.

In some embodiments, the tubing may comprise a tubing connector for fluidly connecting the fresh dialysate supply tubing and the used dialysate waste tubing with the distal end of the patient catheter.

In some embodiments, the PD system may comprise a tubing connector for fluidly connecting the fresh dialysate supply tubing portion and the dialysate waste tubing with the distal end of the patient catheter. Optionally, the tubing connector may be employed for fluidly coupling, in a parallel configuration, the fresh dialysate supply tubing and the waste dialysate waste tubing with the distal end of the patient catheter. For example, the fresh dialysate supply tubing and the waste dialysate waste tubing may be fluidly coupled, in parallel, with the distal end of the patient catheter.

In some embodiments, the concentrate supply device may function as and/or comprise a mixing cavity (e.g., mixing chamber) for mixing concentrate with treated water received from the water treatment device to generate fresh dialysate.

In some embodiments, the water treatment device, the concentrate supply device and/or the tubing disinfectant supply device may be incorporated in the tubing of the PD system. For example, the water treatment device, the concentrate supply device and/or the tubing disinfectant supply device may be incorporated with and/or comprised in the tubing of the PD system. For instance, the water treatment device, the concentrate supply device and/or the tubing disinfectant supply device may be arranged along different sections and embedded by the tubing. The water treatment device, the concentrate supply device and/or the tubing disinfectant supply device may therefore be considered to be arranged "in-line" to the tubing. However, merely for the sake of clarity and without be construed in a limiting manner, the accompanying figures refer to various devices and apparatuses as being "separate" from the tubing, rather than being comprised or embedded in the tubing.

In some embodiments, the tubing disinfectant supply device may function as and/or comprise a mixing cavity (e.g., mixing chamber) for mixing the tubing disinfectant agent, e.g., with water and/or with other carriers suitable for operably distributing the tubing disinfectant agent in the PD system for tubing disinfection purposes.

In some embodiments, the water treatment device comprises a water filter, a water disinfection apparatus, and/or a water conditioning apparatus. The water filter, water disinfection apparatus and/or the water conditioning apparatus may be arranged along different sections and embedded by the tubing of the PD system.

In some embodiments, no recirculation and refreshing of used dialysate may take place with the PD system employed.

In some embodiments, at least some or all components of the PD system that are employed for generating fresh dialysate fluid may be employed as an add-on to (e.g., in-line with) a (manually and/or automatically operable) peritoneal dialysis machine or cycler system, for providing the existing peritoneal dialysis machine with fresh dialysate. The PD system(s) may therefore be configured to provide sufficient amount of fresh dialysate allowing the patient to undergo multiple cycles of continuous cycler-assisted peritoneal dialysis (CCPD) with the existing peritoneal dialysis machine.

In some embodiments, the PD system may provide fresh dialysate for use by a peritoneal dialysis device as described in International Patent Application WO2018142406, filed on 1 Feb. 2018 ("WO2018142406") and which is incorporated by reference herein in its entirety.

In some embodiments, the PD system may provide fresh dialysate to a peritoneal dialysis cycler base, which may be operably coupled with the peritoneal dialysis device, as described in WO2018142406. The fresh dialysate produced by the PD system may be delivered to bags, or directly from the PD system to the peritoneal dialysis device, which is coupled to the cycler base, as for example described in conjunction with FIGS. 14A and 14B of WO2018142406.

In the description of the figures that follows, PD systems are designated by alphanumeric reference "1000". To distinguish between different embodiments of the system, capital alphabetic characters are added after the numerals, for example, PD system 1000A, PD system 1000B, and so forth. However, when there is no need to particularly distinguish between the systems, they are simply and collectively referred to as PD system 1000.

Figure 1:
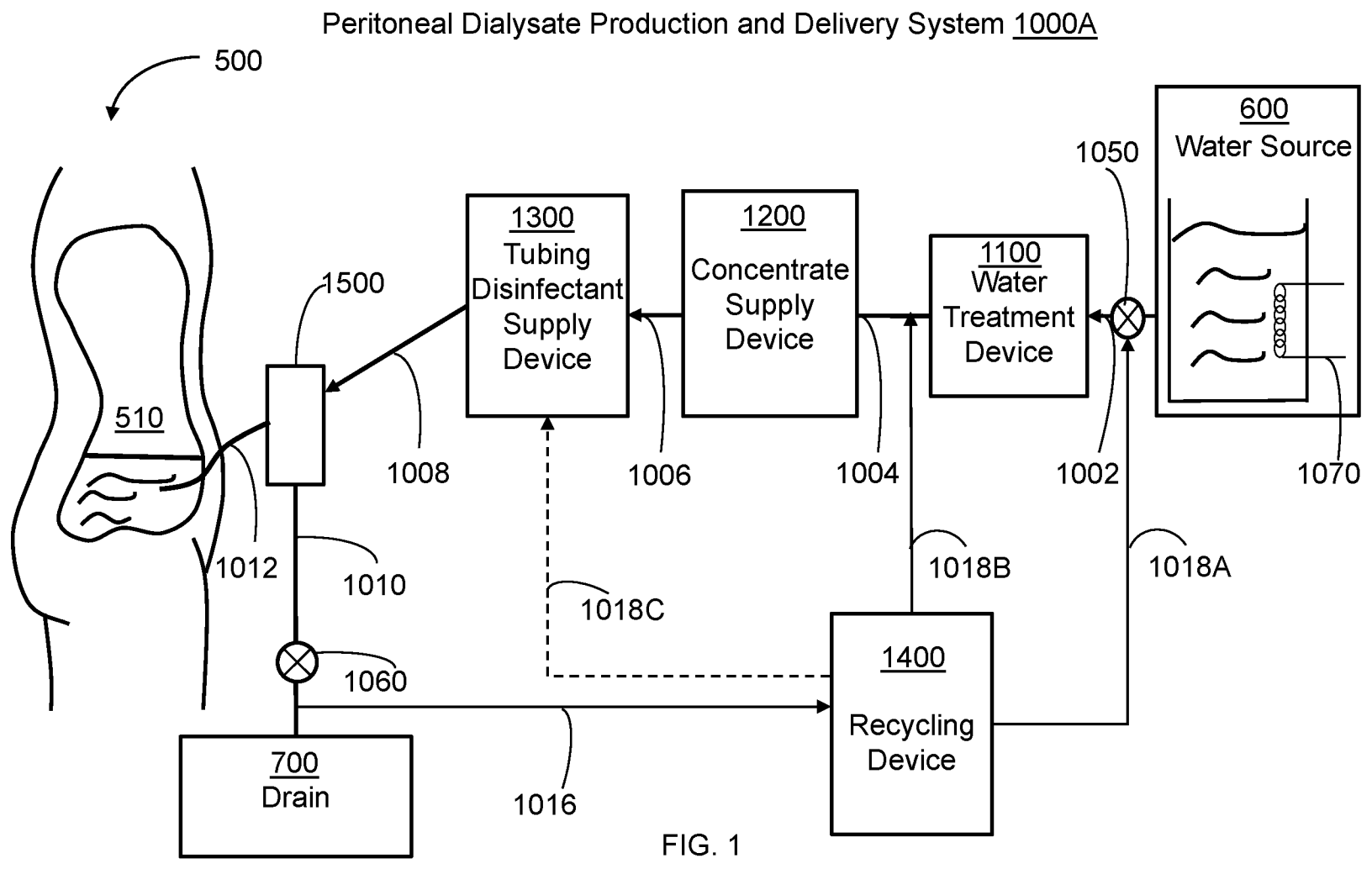

Reference is now made to FIG. 1. In some embodiments, a PD system 1000A for producing and delivering fresh dialysate to a patient 500 comprises a water treatment device 1100 that is and/or that can be coupled with a water source 600 to receive potable water from water source 600, e.g., via a potable supply line (also: source feed water supply line) 1002. Water treatment device 1100 processes received potable water to generate treated water. In some examples, patient 500 and/or water source 600 may not be considered part of a PD system disclosed herein.

In some embodiments, a supply pump device 1050 may be employed for expending energy onto water received from the water source to force water through the PD system for providing the patient with fresh dialysate. In some embodiments, supply pump device 1050 may be implemented as a pump of a dialysis system, the pump being described in International Patent Application WO2017/134657 filed on 1 Feb. 2017 ("WO2017/134657") and which is incorporated herein by reference in its entirety.

Optionally, drain pump 1060, may be a fully automatically operable pump, a semi-automatically operable pump and/or a manually operable pump. Optionally, a manually operable supply pump device 1050 may be a hand-operable air pump implemented by, for example, an expandable and inflatable bag air or bag water pump. Optionally, drainage may be conducted through gravity.

Although supply pump device 1050 is illustrated as being operably positioned at the outlet of water source 600, this should by no means be construed in a limiting manner. Accordingly, supply pump device 1050 may be located at other locations of PD system 1000 suitable for imparting energy onto water for forcing water through the PD system 1000 to provide the patient with fresh dialysate fluid.

In some embodiments, a sanitizing water heater may be employed for purifying water, for instance, by heating the potable water to about 100 degrees Centigrade for a predetermined time (e.g., 2 min). For example, an electric water heater 1070 may be employed for heating water that is present in the PD system to the desired purification temperature. In one example, electric water heater 1070 may be employed at the outlet of the water feed source, upstream to water treatment device 1100.

In some embodiments, the same and/or another water heater may be employed to controllably maintain the temperature of water or fresh dialysate fluid in the PD system to within a predetermined range of, for example, 37±1 degree Centigrade. For example, a heat exchanger (not shown) may be employed for maintaining the temperature of, for example, fresh dialysate fluid. Such heat exchanger may be employed, for example, anywhere along the water and/or fresh dialysate fluid flow path in the PD system.

In some embodiments, water and/or fresh dialysate fluid received by the PD system may be heated by employing a heating chamber (not shown) which is thermally coupled with a flow path of the PD system. The heating chamber contains a substance mixture which is actionable to generate heat in an exothermic chemical reaction for heating water that is present in the flow path.

In some embodiments, PD system 1000A further comprises a concentrate supply device 1200 that is and/or that can be coupled with water treatment device 1100 to be in fluid communication therewith to receive treated water from water treatment device 1100, e.g., via a treated water supply tubing (also: treated water flow path) 1004.

Concentrate supply device 1200 may be operable to add concentrate to generate an osmotic gradient in the water which is required for conducting peritoneal dialysis. Concentrate supply device 1200 may therefore process the treated water to generate fresh dialysate fluid. The concentrate may be in the form of, for example, powder; liquid; and/or gel.

Optionally, the water disinfecting agent may comprise or be gas such as, for example, NOx and/or Ozone.

Optionally, concentrate supply device 1200 may comprise or be implemented as a section of the tubing of PD system 1000A. Optionally, concentrate supply device 1200 may comprise a receptable (e.g., a container, a chamber, a bag) and/or tubing comprising surface portions that are coated with the concentrate and that can come in fluid communication with the treated water for the generation of fresh dialysate fluid. For example, surfaces of the receptacle and/or the tubing of the concentrate supply device 1200 can include inner wall surfaces, tubing surfaces and/or outer surfaces of fin elements extending into the flow path of the treated water to generate fresh dialysate fluid.

In some embodiments, PD system 1000A further comprises a tubing disinfectant supply device 1300 containing and/or operable to receive a tubing disinfectant agent suitable for the disinfection of at least a portion of the inner side walls of tubing lumen extending, for example, from tubing disinfectant supply device 1300 towards the patient.

In some embodiments, tubing disinfectant supply device 1300 may be implemented by a sterilizing fluid dispenser as described in WO2017/134657.

Optionally, tubing lumen that may be disinfected may be of a tubing portion that extends from tubing disinfectant supply device 1300 to a tubing connector 1500 of PD system 1000A into the patient's peritoneal cavity 510.

Optionally, tubing lumen that may be disinfected may be of a tubing portion that extends from tubing disinfectant supply device 1300 to tubing connector 1500, as well as the fluid lumen of the tubing connector.

Optionally, tubing lumen that may be disinfected may be of a tubing portion that extends from tubing disinfectant supply device 1300 to tubing connector 1500 and further of an additional tubing portion 1012 extending from the tubing connector into the patient's peritoneal cavity 510, including the fluid lumen of tubing connector 1500. The additional tubing portion may also be referred to as "patient catheter". Patient catheter 1012 has a proximal end for positioning thereof inside the patient body, and a distal end which may be operably coupled with connector 1500 for bringing connector 1500 in fluid communication with the patient's peritoneal cavity 510. Optionally, proximal end may be part of a catheter port, and the distal end may be part of an external catheter portion. For example, patient catheter 1012 may have a two disconnectable portions, namely the catheter port and the external catheter portion.

In some embodiments, tubing connector 1500 may be implemented by an automatic connector device as described in WO2017/134657 or as the device described in WO2018142406.

Optionally, tubing disinfectant supply device 1300 may be operable to provide (e.g., distribute) the tubing disinfectant agent for the disinfection of at least some of a fresh dialysate fluid flow path and/or of additional water flow path sections of PD system 1000A.

Optionally, tubing disinfectant supply device 1300 may comprise or be implemented as a section of the tubing of PD system 1000A. Optionally, tubing disinfectant supply device 1300 may comprise a receptable (e.g., a container, a chamber, a bag) and/or tubing comprising surface portions that are coated or otherwise provided with the tubing disinfectant agent and that can come in fluid communication with water flowing through the tubing disinfectant supply device for delivering the tubing disinfectant agent to the desired flow path sections (e.g., tubing portions or sections). Surfaces of the receptacle and/or the tubing of the tubing disinfectant supply device 1300 can include inner wall surfaces, tubing surfaces and/or outer surfaces of fin elements extending into the flow path of water flowing through the tubing disinfectant supply device. Water may therefore serve as carrier for supplying (e.g., distributing) the tubing disinfectant agent to the desired tubing portions. Other carriers may be also be employed for supplying (e.g., distributing) the tubing disinfectant agent to the desired flow path sections (e.g., tubing sections).

In the example shown schematically in FIG. 1, concentrate supply device 1200, tubing disinfectant supply device 1300 and tubing connector 1500 are fluidly coupled in series with each other. Hence, in some embodiments, tubing disinfectant supply device 1300 may receive fresh dialysate fluid that may be mixed with the tubing disinfecting agent. In some other embodiments, tubing disinfectant supply device 1300 may supply tubing disinfecting agents without mixing thereof with fresh dialysate fluid.

PD system 1000A may further be configured to allow draining of used dialysate to drain 700 via dialysate drain or waste tubing (also: waste flow path) 1010. In some embodiments, dialysate waste tubing 1010 may be in fluid communication with patient catheter 1012 to enable drainage of used peritoneal dialysate, via patient catheter 1012, to drain 700. Optionally, dialysate waste tubing 1010 may be in fluid communication with patient catheter 1012 via tubing connector 1500.

In some embodiments, PD system 1000 may comprise a drain pump 1060 suitable for imparting energy onto used dialysate fluid for drainage thereof from the peritoneal cavity 510 via waste tubing 1010 to drain 700. Optionally, drain pump 1060, may be an automatically operable pump, a semi-automatically operable pump and/or a manually operable pump. Optionally, drain pump 1060 may be a hand-operable air pump implemented by, for example, an expandable and inflatable bag air or bag water pump.

In some embodiments, PD system 1000 may comprise a used dialysate recycling device 1400 configured to recycle at least some or all of the used dialysate to produce recycled feed water. Hence, instead of draining used dialysate, at least some or all of the used dialysate may be recycled by recycling device 1400.

Recycling device 1400 may be configured to generate water of sufficient quality suitable for further treatment by water treatment device 1100 and/or concentrate supply device 1200 to generate fresh dialysate. In some examples, the process of recycling used dialysate water may only be performed when PD system 1000 is disconnected from patient 500. In some other examples, the process of recycling may be performed while PD system 1000 is operably coupled with patient 500. In some further examples, the process of recycling may be performed while PD system 1000 is coupled with patient 500 via catheter 1012 yet the fluid pathway in PD system 1000 for delivering fresh dialysate to peritoneal cavity 510 is interrupted (e.g., blocked).

Used dialysate may be delivered to recycling device 1400 via piping 1016, and from recycling device 1400 towards water treatment device 1100 via piping 1018A (e.g., for the addition of softeners) or to concentrate supply device 1200 via piping 1018B (e.g., if a sensor has measured that the recycled water is soft enough allowing skipping of the softener stage). In some embodiments, may be delivered via gravitation or by actively expending energy onto used dialysate and/or recycled water, by a pump.

Recycling device 1400 may be configured to recycle used dialysate water without the employment of an external power source and/or with the employment of a comparatively low-power energy source. For example, recycling device 1400 may be configured to recycle used dialysate by employing, for example, chemical-based (e.g., sorbent-based), filtration, centrifugal separation, coagulation, aerobic, anaerobic, crystallization, distillation, solvent extraction, oxidation, precipitation, ion exchange, micro- and/or ultrafiltration, reverse osmosis, absorption, adsorption, electrolysis, electrodialysis and/or other water regeneration and/or recycling technologies.

Considering the number of times the PD system may self-sufficiently perform peritoneal dialysis treatment cycles, the recycling of used dialysate water may reduce consumption of fresh source feed water or render providing water treatment device 1100 with fresh source feed water superfluous to generate fresh dialysate the number of times the PD system is configured to self-sufficiently produce fresh-dialysate.

In some embodiments, used dialysate can be recycled at least, for example, 2, 3, 5, 10, 15, 20, or 100 times to produce recycled feed water, which may be processed to produce fresh dialysate, until the agents and/or equipment used by recycling device 1400 must be replaced or refreshed.

In some embodiments, a certain amount of fresh source feed water may be admixed to recycled dialysate water, during each or only after at number of recycling passes through recycling device 1400, for example, to reduce the consumption of agents employed by recycling device 1400.

In some embodiments, the recycling stage may be automatically controlled by one or more sensors configured to sense one or more characteristics of used dialysate water and/or recycled dialysate water.

In some embodiments, the recycling stage may be performed without involving control automation.

Water treatment device 1100 may comprise a water filter (e.g., sand), a water disinfection apparatus and a water conditioning apparatus which may be in fluid communication with each other in various configurations, for example as shown schematically in FIGS. 2A-C.

The recycled feed water may be recirculated back into water treatment device 1100, for example, for recycled water disinfection, conditioning and/or filtering purposes.

In some examples, recycled feed water (as well as source feed water) produced by recycling device 1400 may be selectively delivered to one or more of a water filter apparatus 1120, water disinfection apparatus 1140 or water conditioning apparatus 1160 of water treatment device 1100.

In some embodiments, part of the recycled feed water may be provided to tubing disinfectant supply device 1300 via piping 1018C to flush at least part of the PD system with disinfectant.

In some embodiments, a PD system 1000 may be operable to provide an output indicating the status (e.g., start/completion) of a water treatment stage employed by water treatment device 1100.

It is noted that the description of embodiments in FIG. 1 are analogously applicable to all PD system configurations described herein with respect to FIGS. 2-16.

In some embodiments, as shown in FIG. 2A, a water treatment device 1100A may comprise a water filter apparatus (or simply: water filter) 1102 that is operable to receive potable water from source feed water supply line 1002. Water filter apparatus 1120 may be operable to reduce the impurities concentration that may be present in potable water and comprise a filtration medium such as, for example, a strainer, sponge-like material, granulates (e.g., sand), resin, carbon (e.g., activated carbon), ceramic material, a semipermeable membrane, and/or the like.

In some embodiments, PD system 1000 may comprise at least one sensor operably coupled along a water flow path in the PD system for measuring values of water characteristics (e.g., parameters). Such water characteristic values can include, for example, the level or concentration of impurities in water to provide an indication of water treatment efficiency, the level or concentration of osmotic agent in water, flow rate, water pressure and/or water temperature.

In some embodiments, water treatment device 1100A may further comprise a water disinfection apparatus 1140 suitable for disinfecting water. Water disinfection apparatus 1140 may be, via a flow path 1101, in downstream fluid communication with water filter apparatus 1120 supplying filtered water. For example, water disinfection apparatus 1140 be operative to provide a water disinfecting agent such as, for example, hypochlorite e.g., of sodium and/or calcium, chlorine dioxide, free chlorine, chloramine, ozone; solutes (e.g., Na, Cl, Ca) and/or acids to deactivate microorganisms present in the water to obtain disinfected water.

Optionally, water disinfection apparatus 1140 may contain one or more water disinfecting agents and may be configured such that water disinfecting agents are added to water entering disinfection apparatus. For example, water disinfection apparatus 1140 may comprise a receptacle (e.g., a container) and/or tubing for receiving water from water filter apparatus 1120. At least some surfaces of the receptacle and/or the tubing may be coated with the disinfection agent such that at least some of the water disinfection agent is added (e.g., mixed) to filtered water flowing over these surfaces. Surfaces of the receptacle and/or the tubing can include inner wall surfaces, tubing surfaces and/or outer surfaces of fin elements extending into the flow path of the filtered water.

The water disinfecting agent may be in the form of, for example, powder; liquid, and/or gel, and may be coated on to the walls of the disinfection container.

Optionally, water disinfection apparatus 1140 may comprise an ultraviolet light source configured to disinfect water. For example, UV light sources (e.g., one or more LED UV lamps) may be arranged to irradiate water flowing in tubing of water disinfection apparatus 1140 for disinfection. Additional or alternative radiation energy sources may be employed for disinfecting water.

In some examples, UV light sources may be employed that are configured to irradiate water with enough UV radiation energy to reduce the concentration of water disinfecting agents in the water.

In some embodiments, UV light sources may be employed to remove water disinfecting agents contained in water to reduce water disinfectant concentration to below a desired level.

In some embodiments, water treatment device 1100A may comprise a water conditioning apparatus 1160 which is in fluid communication, via a flow path 1102 with water disinfection apparatus 1140, downstream of the disinfection apparatus. Water conditioning apparatus 1160 may be operable to provide treated water at the outlet of water treatment device 1100.

Optionally, water conditioning apparatus 1160 may comprise chemical and/or non-chemical softeners. Chemical softeners may include, for example, the employment of an ion-exchange resin in which hardness ions are exchanged for sodium ions. Non-chemical softeners may be operable to reduce hardness of water by subjecting it to an electrically-induced dissociation process (also: electrolysis) to obtain a desired hardness level.

Optionally, water conditioning apparatus 1160 may be operable to remove water disinfectants, supplied by water disinfection apparatus 1140, from disinfected water. For example, water disinfectant may be removed to reduce their concentration to drop below a desired level, and to obtain desired pH requirements (e.g., 5.0-7.0). Removal of a disinfection agent may be achieved, for example, by employing mechanical filtration, a chemical reaction (e.g., chemical absorption), and/or adsorption.

Optionally, water conditioning apparatus 1160 may only be operable to reduce concentration of water disinfectants, but not to be operable to reduce water hardness. Hence, in some embodiments, a PD system may be free of a water hardness reducing apparatus.

In some embodiments, water conditioning apparatus 1160 may be fluidly coupled with concentrate supply device 1200 such that water supplied by water conditioning apparatus 1160 is received by concentrate supply device 1200 for the generation of fresh dialysate fluid.

Reference is now made to FIG. 2B. A water treatment device 1100B may comprise a water disinfection apparatus 1140 that may be fluidly coupled with source feed water supply line 1002. Water filter apparatus 1120 may be in downstream fluid communication with water disinfection apparatus 1140 via a flow path 1103, and water conditioning apparatus 1160 may be in downstream fluid communication via a flow path 1104 with water filter apparatus 1120. Water conditioning apparatus 1160 may be operable to provide treated water at the outlet of water treatment device 1100B.

Reference is now made to FIG. 2C. A water treatment device 1100C comprises water disinfection apparatus 1140 that may be fluidly coupled with source feed water supply line 1002.

In some embodiments, an apparatus 1180 having combined water filter and preconditioning functionality may be in downstream fluid communication via a flow path 1105 with water disinfection apparatus 1140. Combined water filter & preconditioning apparatus 1180 may be operable to provide treated water at the outlet of water treatment device 1100C.

Reference is now made to FIG. 2D. A water treatment device 1100D comprises water disinfection apparatus 1140 that may be fluidly coupled with source feed water supply line 1106 via flow path 1002.

Water conditioning apparatus 1160 may be in downstream fluid communication via flow path 1106 with water disinfection apparatus 1140. Water filter apparatus 1120 may be in downstream fluid communication with water conditioning apparatus 1160 via flow path 1107. Water filter apparatus may be operable to provide treated water at the outlet of water treatment device 1100D.

As will be outlined herein below in greater detail, a peritoneal dialysis cycle may comprise, in some embodiments, a tubing disinfection stage, a used dialysate drain stage, and a fresh dialysate delivery stage. With respect to the sequence of stage, the used dialysate drain stage may precede the fresh dialysate delivery stage. Alternatively, the fresh dialysate delivery stage may precede the used dialysate drain stage. In some embodiments, the tubing disinfection stage may be employed prior to the fresh dialysate delivery stage and after the used dialysate drain stage.

Optionally, tubing disinfection may be employed prior to each fresh dialysate fluid delivery stage. Optionally, tubing disinfection may be employed only after completion of two or more cycles of fresh peritoneal fluid delivery, osmosis/diffusion stage (also: ultrafiltration) and used peritoneal dialysate drainage.

In view of the above, the following may be considered valid peritoneal dialysis cycles:

First Option:
    I) used dialysate drain stage;
    II) tubing disinfection stage; and
    III) fresh dialysate delivery stage Second Option:
    I) tubing disinfection stage;
    II) fresh dialysate delivery stage; and
    III) used dialysate drain stage.

Third Option:
    I) fresh dialysate delivery stage;
    II) used dialysate drain stage; and
    III) tubing disinfection stage.

In some embodiments, a recycling stage may be employed instead or in addition to employing a used dialysate drain stage.

It is therefore noted that the dialysis stages described herein in conjunction with the accompanying figures below may be different and should therefore by no means be construed in a limiting manner.

An osmosis/diffusion stage to allow waste, toxins and excess water to pass across the peritoneal membrane, due to osmosis and/or diffusion, from the patient's bloodstream into the dialysate, is considered to be employed following each fresh dialysate delivery stage. Merely for the sake clarity, the mechanisms of the osmosis/diffusion stage are not described herein in further detail.

In some embodiments, in the figures, flow paths illustrated with solid lines may be considered "active", flow paths illustrated with dashed lines are considered "idle" or "inactive", and flow paths illustrated with round dots are considered as "optionally in use". However, it is noted that the above noted different "dash type" of lines should by no means be construed in a limiting manner. Accordingly, although some illustrations may pertain a flow path as "optional", it may in certain embodiments be considered as "always in-use", "never in use"; and flow paths indicated as "active" may, in some embodiments, be "inactive", or vice versa.

Reference is now made to FIGS. 3-6, exemplifying a peritoneal dialysate cycle that may be employed with PD system 1000A.

Figure 3:
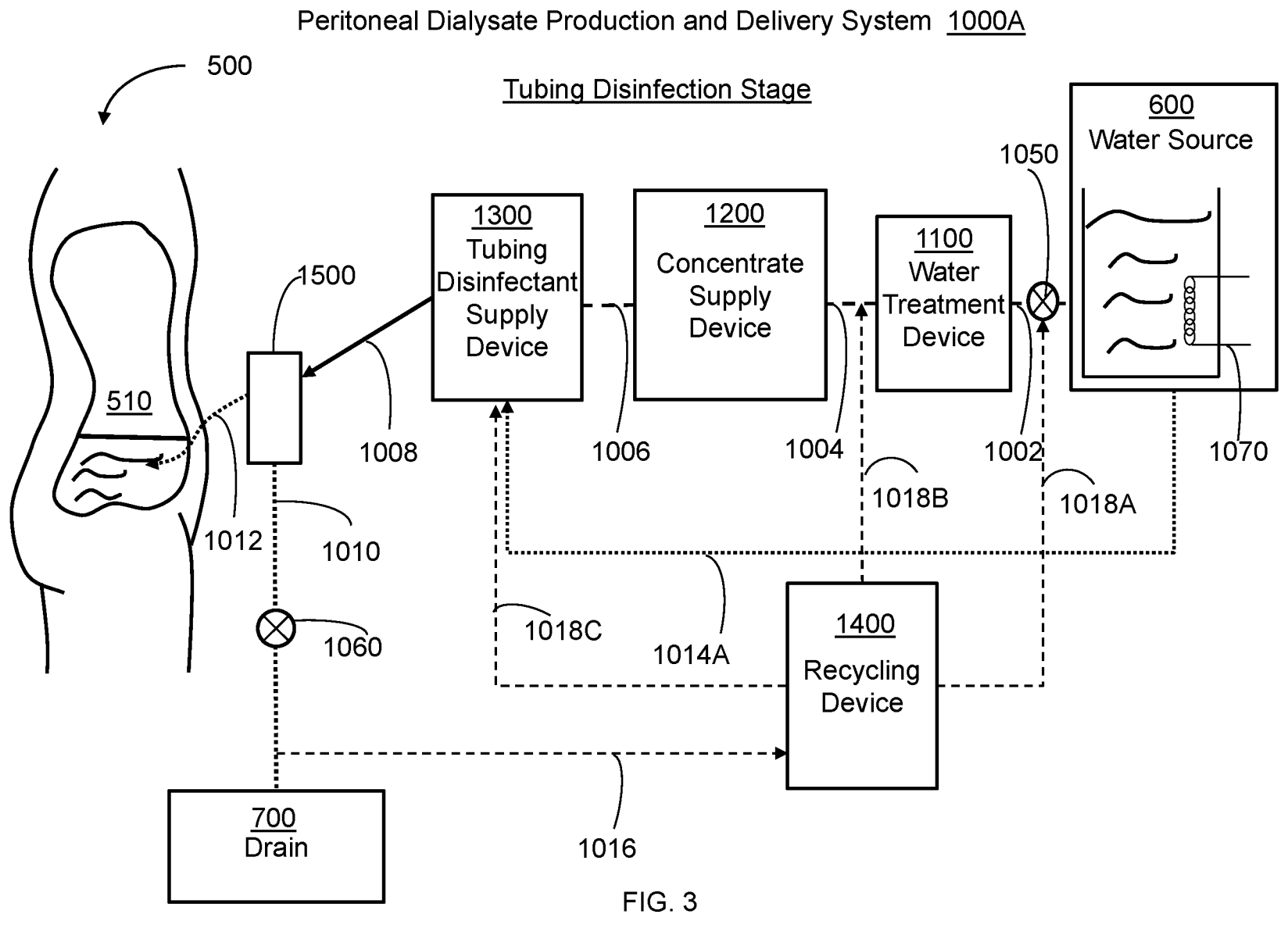

FIG. 3 exemplifies, schematically, a tubing disinfection stage in which a tubing disinfecting agent is supplied to disinfect a flow path 1008 defined by tubing leading from tubing disinfectant supply device 1300 up to and, optionally, including tubing connector 1500. In some embodiments, the tubing disinfection stage may also include supplying tubing disinfecting agent to at least a portion of the patient catheter flow path (also: patient catheter) 1012. For instance, a tubing disinfecting agent may be supplied to the external catheter portion and, optionally, also through the catheter port for disinfecting the flow path that leads up to peritoneal cavity 510.

As schematically shown in FIG. 3, flow paths 1002, 1004 and 1006 may in some embodiments be "active", and in some embodiments "inactive".

When active, source feed water may be supplied through flow paths 1002, 1004 and 1006 to tubing disinfectant supply device 1300 for mixing the tubing disinfecting agent with water provided by concentrate supply device 1200 in the tubing disinfection stage. This process may continue until no additional tubing disinfecting agent is added to the fresh dialysate fluid. This may be the case when all tubing disinfecting agent has been used up. Actively controllable (e.g., electrically powered) water treatment processes that may be employed by water treatment device 1100, and/or actively controllable processes for providing concentrate by concentrate supply device 1200 may be selectively controlled to remain either active (i.e., provide concentrate to water) or inactive (i.e., not providing concentrate or providing a negligible amount) during the tubing disinfection stage. Accordingly, water provided by concentrate supply device 1200 in the tubing disinfection stage may in some embodiments not qualify as fresh dialysate fluid, and in some embodiments it may qualify as fresh dialysate fluid, which may then later be mixed with the tubing disinfecting agent. In one example, fresh dialysate fluid that may be mixed with tubing disinfecting agent may still qualify as fresh dialysate fluid. In another example, fresh dialysate fluid that may be mixed with the tubing disinfecting agent may no longer qualify as fresh dialysate fluid. Whether a mixture of fresh dialysate fluid with the tubing disinfecting agent still qualifies as fresh dialysate fluid or not, may for example depend on the type of tubing disinfecting agent used and/or on concentration of disinfecting tubing agent in the fresh dialysate water. For example, a disinfectant-water mixture may be used be used a fresh dialysate fluid if the concentration value is 110 MEQ/L or lower.

In some embodiments, source feed water may be supplied to tubing disinfectant supply device 1300 while bypassing flow paths 1002, 1004 and 1006 by a bypass flow path 1014A for mixing with the tubing disinfecting agent for use of the source water-disinfectant mixture for tubing disinfection. Optionally, source feed water mixed with the disinfecting agent may not qualify as fresh dialysate fluid.

In some embodiments, the tubing disinfecting agent and/or the tubing disinfecting agent mixed with water that does not qualify as fresh dialysate may be supplied via flow path 1008, connector 1500 and waste flow path 1010 to drain 700.

In another example, the tubing disinfecting agent and/or water that may or may not qualify as fresh dialysate fluid, when mixed with the tubing disinfecting agent, may be supplied to flow path 1008, connector 1500 and at least a portion of patient catheter 1012 (e.g., external catheter and/or catheter port), if the external catheter portion is not in fluid communication with the catheter port.

In some embodiments, water that may qualify as fresh dialysate fluid even when mixed with the tubing disinfecting agent may be supplied through flow path 1008, connector 1500 and patient catheter 1012 to peritoneal cavity 510 for use in an osmosis/diffusion stage and for subsequent used dialysate drain stage. In this example, the tubing disinfection stage may be identical to the fresh dialysate delivery stage.

In some embodiments, the tubing disinfecting agent mixed with water that does qualify as a fresh peritoneal dialysis fluid may be provided to peritoneal cavity 510 for a comparatively short period of time, from where it may be drained when tubing disinfection may be considered completed.

Figure 4:
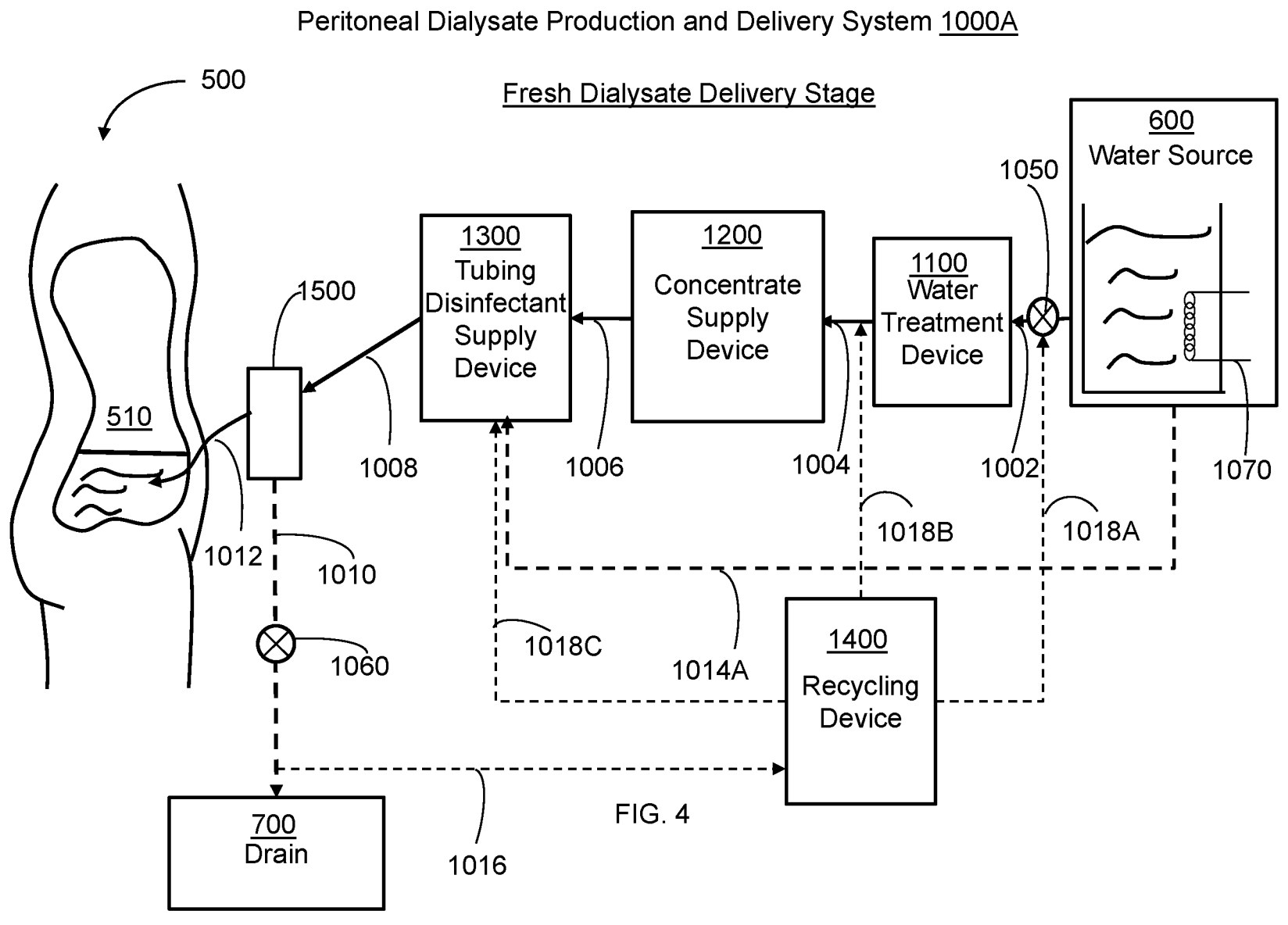

Additional reference is made to FIG. 4. According to some embodiments, upon completion of the tubing disinfection stage, fresh dialysate delivery stage may be employed. During the fresh dialysate delivery stage, feed water supply may be supplied to water treatment device 1100 to generate treated water at the water treatment device outlet, and further through concentrate supply device 1200 to generate fresh dialysate fluid, which is then forced via tubing disinfectant supply device 1300 and connector 1500 to the patient's peritoneal cavity 510. As already indicated herein, in the fresh dialysate delivery stage, tubing disinfectant supply device 1300 may or may not be active. When inactive, no tubing disinfecting agents or a negligible amount of tubing disinfecting agents may be mixed with the fresh dialysate fluid. When active, an amount of tubing disinfecting agents that is mixed with or added to the fresh dialysate fluid is sufficient for tubing disinfection and also allows for supplying the mixture of the tubing disinfecting agent and fresh dialysate fluid to the patient's peritoneal cavity 510 retain in the peritoneal cavity for a dwell time period in the osmosis/diffusion stage (also: ultrafiltration stage) to allow for osmosis and/or diffusion through the peritoneal membrane to occur during which fresh dialysate fluid is replaced with used dialysate fluid.

Figure 5:
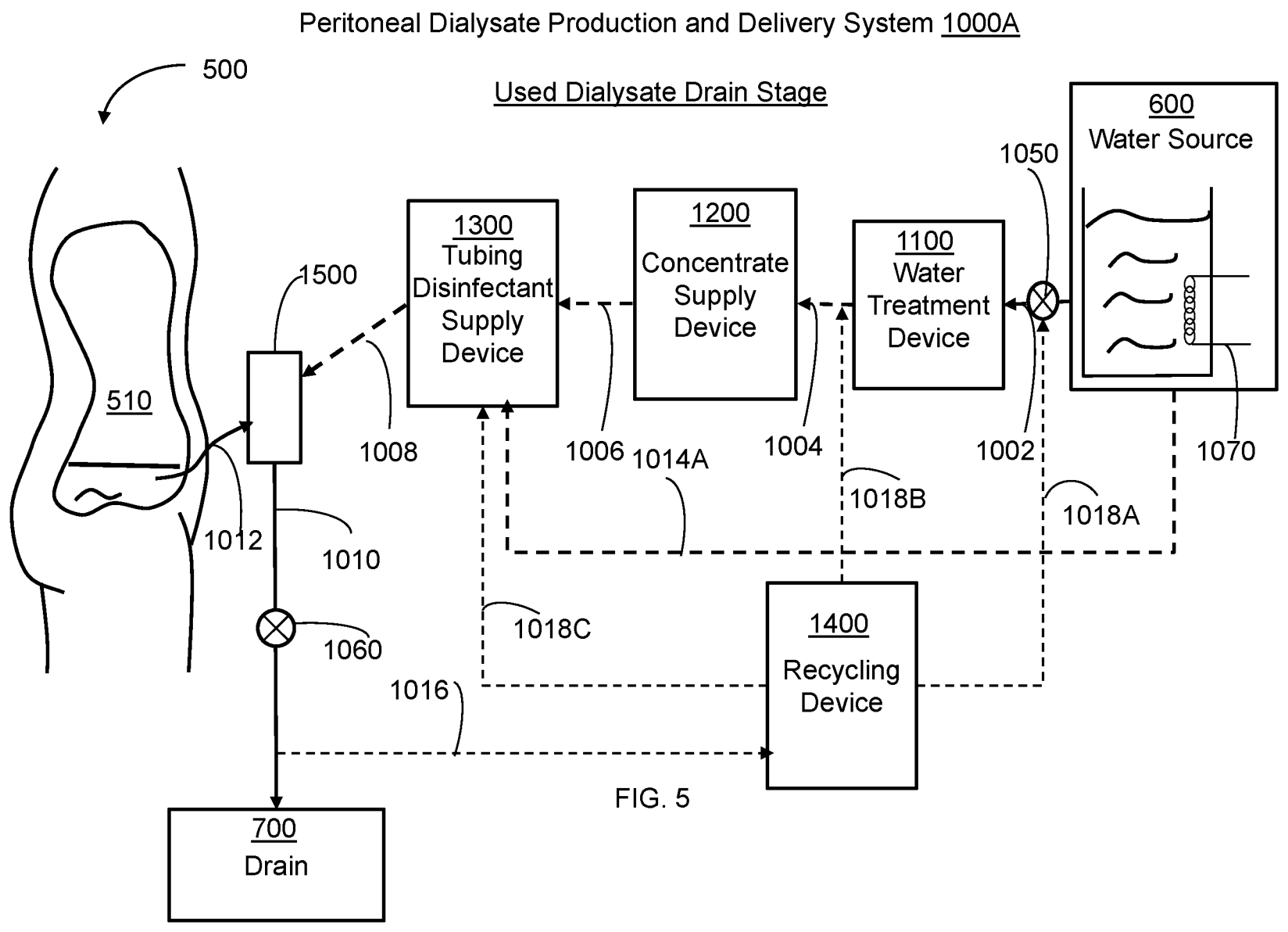

Additional reference is now made to FIG. 5. Used peritoneal dialysate may be drained from peritoneal cavity 510 via patient catheter 1012, connector 1500 and waste tubing 1010 to drain 700.

Further referring to FIG. 6, a used dialysate recycling stage may be employed instead of or in addition to the used dialysate drain stage.

In some embodiments, all of used dialysate may be recycled by recycling device 1400.

In some embodiments, a portion of the used dialysate may be drained, e.g., to flush out a certain amount of waste, and another portion may be recycled by recycling device 1400.

At least some of the recycled feed water may be delivered to water treatment device 1100 (e.g., to soften the water) via piping 1018A; to concentrate supply device 1200 via piping 1018B and/or to tubing disinfectant supply device 1300 (e.g., for disinfecting at least some of the PD system) via piping 1018C.

The amount of used dialysate may be controlled for example, via a controllable shunt valve (not shown) and based on sensor output provided by sensors (not shown) measuring various characteristics of the used dialysate water.

At least some of the recycled feed water may be delivered to water treatment device 1100 (e.g., to soften the water) via piping 1018A; to concentrate supply device 1200 via piping 1018B and/or to tubing disinfectant supply device 1300 (e.g., for disinfecting at least some of the PD system) via piping 1018C.

Figure 7:
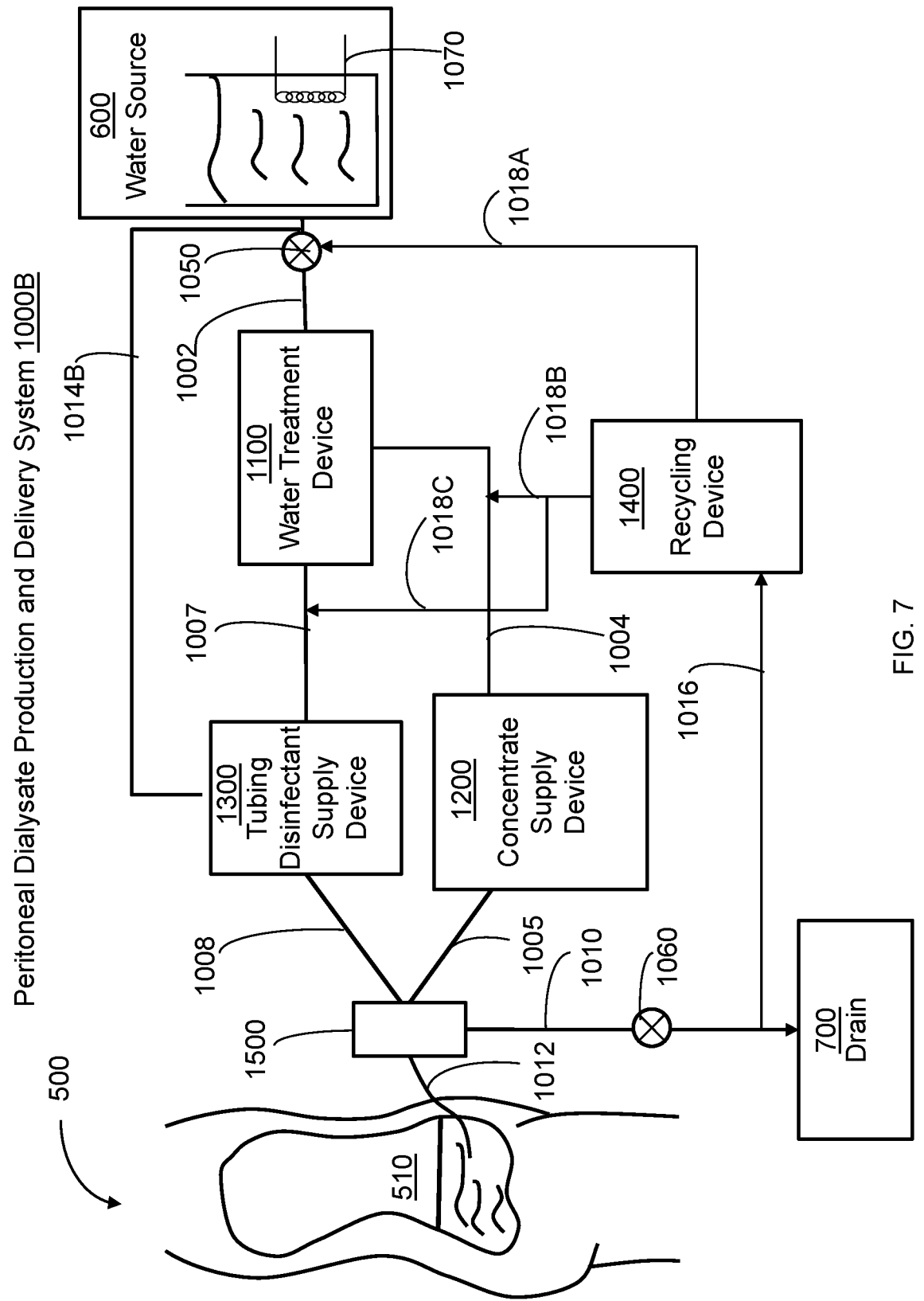
FIG. 7 a schematic illustration of a peritoneal dialysate production and delivery system, according to some other embodiments.

Reference is now made to FIG. 7. In some embodiments, in a PD system 1000B, concentrate supply device 1200 and tubing disinfectant supply device 1300 may be in fluid communication, in a parallel coupling configuration, with and upstream to connector 1500, for example, via flow paths 1005 and 1008.

Water treatment device 1100 may be coupled to feed water source 600 such to be in fluid communication with the feed water source via a flow path 1007. In addition, water treatment device 1100 may be in fluid communication with concentrate supply device 1200 and tubing disinfectant supply device 1300 in a parallel coupling configuration. Water treatment device 1100 may be coupled upstream to concentrate supply device 1200 and tubing disinfectant supply device 1300.

In some embodiments, analogous to PD system 1000A, PD system 1000B may comprise a bypass flow path 1014B that directly connects water source 600 with tubing disinfectant supply device 1300 by bypassing water treatment device 1100.

Further reference is made to FIG. 8. In some embodiments, a tubing disinfection stage may comprise supplying the tubing disinfecting agent from tubing disinfectant supply device to the desired tubing portions. Analogous to PD system 1000A, desired tubing portions may include at least some of flow path 1008, at least some of the tubing comprised in connector 1500, and/or at least some of the tubing of patient catheter 1012.

Optionally, the tubing disinfecting agent may be supplied to tubing portions to be disinfected without mixing of the agent, for instance, with additional water and/or other compositions.

Optionally, feed water supply may be supplied without further treatment, e.g., via bypass flow path 1014B, to tubing disinfecting supply device 1300 for mixing thereof with the tubing disinfecting agent. The mixture of feed water and tubing disinfecting agent may then be supplied to the desired tubing portions for tubing disinfection.

Optionally, feed water supply may be supplied to water treatment device 1100 via flow path 1002 for treatment to generate treated water, which may then be supplied via flow path 1007 to tubing disinfectant supply device 1300 for mixing thereof with the tubing disinfecting agent. The mixture of treated water and tubing disinfecting agent may then be supplied to the desired tubing portions for tubing disinfection.

Optionally, fresh dialysate fluid may be generated which may be delivered to combined connector & tubing disinfectant supply device 1301 for mixing with the tubing disinfecting agent and delivery to desired tubing portions.

Optionally, tubing disinfection may comprise delivering treated water to desired tubing portions.

Further referring to FIG. 9, a fresh dialysate delivery stage may be employed which may comprise supplying feed water supply to water treatment device 1100 to obtain treated water. Treated water may then be supplied, via treated water flow path 1004, to concentrate supply device 1200 to generate fresh dialysate fluid for delivery to peritoneal cavity 510. As shown in FIG. 9, due to the parallel coupling configuration, the flow paths for supplying treated and/or feed water to tubing disinfectant supply device 1300 are separate from the flow path used to supply treated water to concentrate supply device 1200. Hence, the chances of mixing the tubing disinfecting agent with fresh dialysate fluid may be reduced, minimized or eliminated.

In some embodiments, following the supply of fresh dialysate to peritoneal cavity 510, an osmosis/diffusion stage may be employed in which used dialysate fluid replaces fresh dialysate fluid in peritoneal cavity 510.

Additional reference is made to FIG. 10. A used dialysate drain stage may be employed to drain used dialysate from peritoneal cavity 510. Analogous to what has been described with respect to PD system 1000A, used peritoneal dialysate may be drained from peritoneal cavity 510 via patient catheter 1012, connector 1500 and waste tubing 1010 to drain 700.

Further referring to FIG. 11, a used dialysate recycling stage may be employed instead of or in addition to the used dialysate drain stage.

In some embodiments, all of used dialysate may be recycled by recycling device 1400.

In some embodiments, a portion of the used dialysate may be drained, e.g., to flush out a certain amount of waste, and another portion may be recycled by recycling device 1400.

At least some of the recycled feed water may be delivered to water treatment device 1100 (e.g., to soften the water) via piping 1018A; to concentrate supply device 1200 via piping 1018B and/or to tubing disinfectant supply device 1300 (e.g., for disinfecting at least some of the PD system) via piping 1018C.

The amount of used dialysate may be controlled for example, via a controllable shunt valve (not shown) and based on sensor output provided by sensors (not shown) measuring various characteristics of the used dialysate water.

Figure 12:
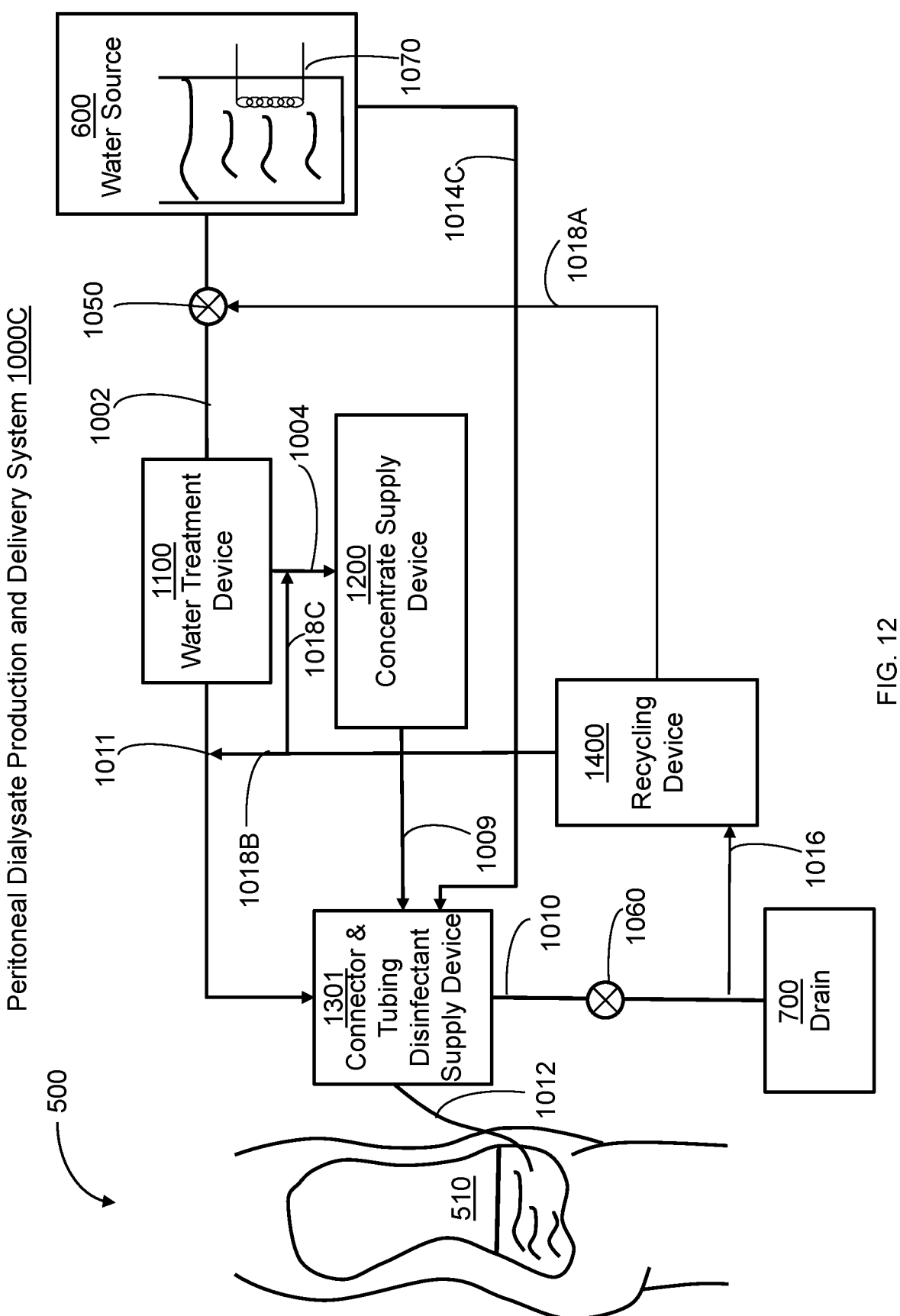
FIG. 12 a schematic illustration of a peritoneal dialysate production and delivery system, according to some alternative embodiments.

Additional reference is now made to FIG. 12. In some embodiments, in a PD system 1000C, a combined connector & tubing disinfectant supply device 1301 may be employed which may be configured to both function as a connector (e.g., tubing manifold), similar for instance to what has been outlined herein with respect to PD systems 1000A and 1000B, as well as a tubing disinfectant supply device. For instance, device 1301 may be implemented or comprise a connector that may comprise the tubing disinfecting agent which may, for example, be provided on surfaces of the connector tubing that may come into contact with fluid (e.g., feed water, treated water or fresh dialysate fluid) delivered to the connector. Such surfaces of device 1301 may include, for example, include inner wall surfaces, tubing surfaces and/or outer surfaces of fin elements that may be configured to engage with water flowing in manifold & tubing disinfectant supply device 1301.

Figure 13:
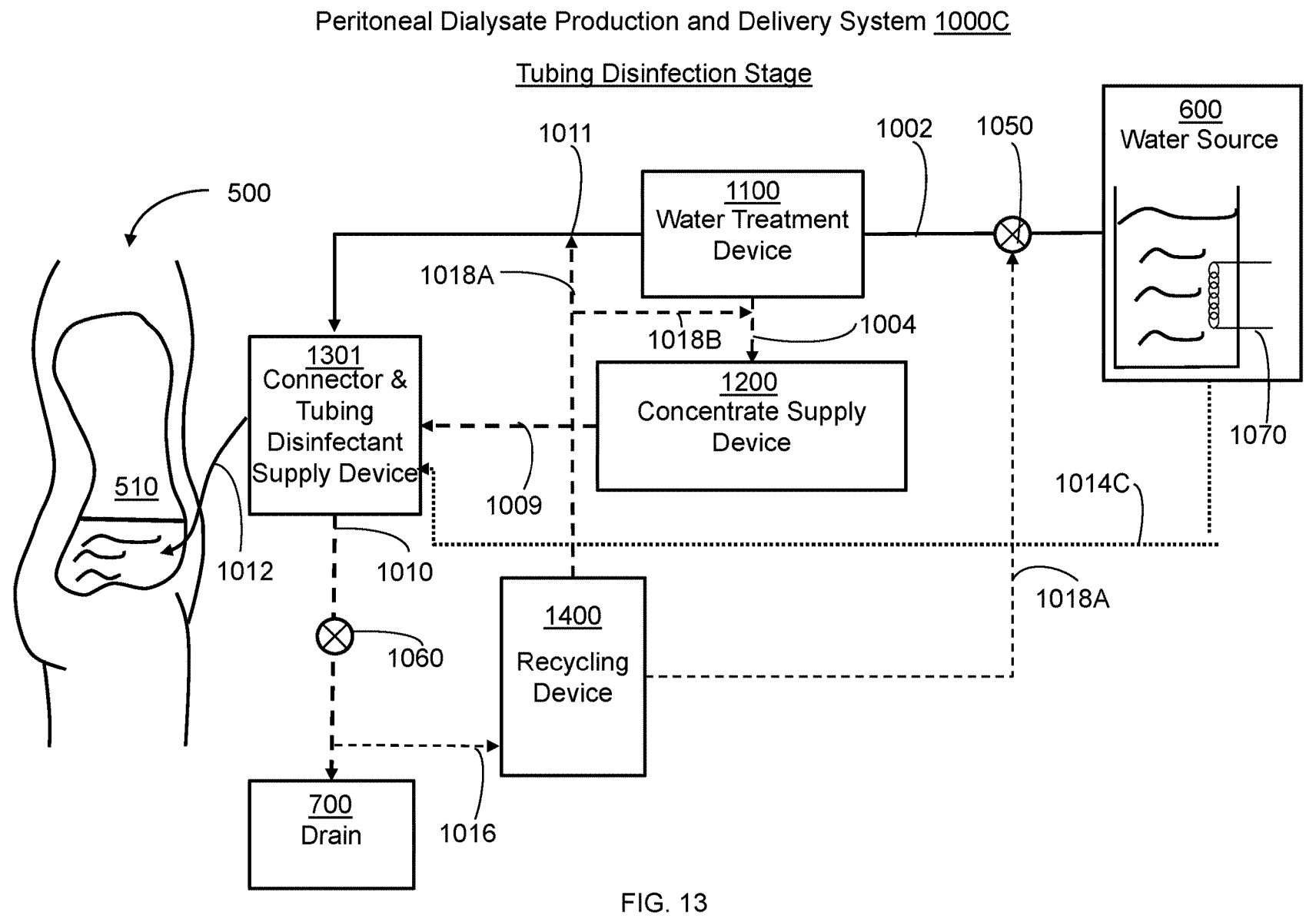

Referring now to FIG. 13, a tubing disinfectant stage may comprise supplying the tubing disinfecting agent from the tubing disinfectant supply device to the desired tubing portions. Analogous to PD systems 1000A and 1000B, desired tubing portions may comprise delivering the tubing disinfecting agent to tubing comprised in the combined connector & tubing disinfectant supply device 1301 and to at least some of the tubing of patient catheter 1012.

Optionally, tubing disinfectant agents may be supplied to tubing portions to be disinfected without mixing of the disinfection agent with water and/or other compositions.

Optionally, feed water supply may be supplied without further treatment, e.g., via bypass 1014C, to connector & tubing disinfectant supply device 1301 for mixing of the feed water supply with the tubing disinfecting agent. The mixture of feed water and the tubing disinfecting agent may then be supplied to the desired tubing portions for tubing disinfection.

Optionally, feed water supply may be supplied to water treatment device 1100 via flow path 1002 for treatment to generate treated water, which may then be supplied via flow path 1011 to tubing disinfectant supply device 1300 for mixing thereof with the tubing disinfecting agent. The mixture of treated water and the tubing disinfecting agent may then be supplied to the desired tubing portions for tubing disinfection.

Optionally, fresh dialysate fluid may be generated which may be delivered to connector & tubing disinfectant supply device 1301 for mixing with the tubing disinfecting agent and delivery to desired tubing portions.

Optionally, tubing disinfection may comprise delivering treated water to desired tubing portions.

Further referring to FIG. 14, a fresh dialysate delivery stage may be employed which may comprise supplying feed water supply to water treatment device 1100 to obtain treated water. Treated water may then be supplied, via treated water flow path 1004, to concentrate supply device 1200 to generate fresh dialysate fluid for delivery to peritoneal cavity 510 via flow path 1009, combined connector & tubing disinfectant supply device 1301 and patient catheter 1012. As shown in FIG. 13, due to the parallel coupling configuration, the flow paths for supplying treated and/or feed water to connector & tubing disinfectant supply device 1301 may be separate from the flow path used to supply treated water to concentrate supply device 1200 and also different from the flow path for supplying fresh dialysate fluid to connector & tubing disinfectant supply device 1301. Hence, the chances of mixing the tubing disinfectant agent with fresh dialysate fluid may be reduced, minimized or eliminated.

In some embodiments, following the supply of fresh dialysate to peritoneal cavity 510, an osmosis/diffusion stage may be employed in which used dialysate fluid replaces fresh dialysate fluid in peritoneal cavity 510.

Figure 15:
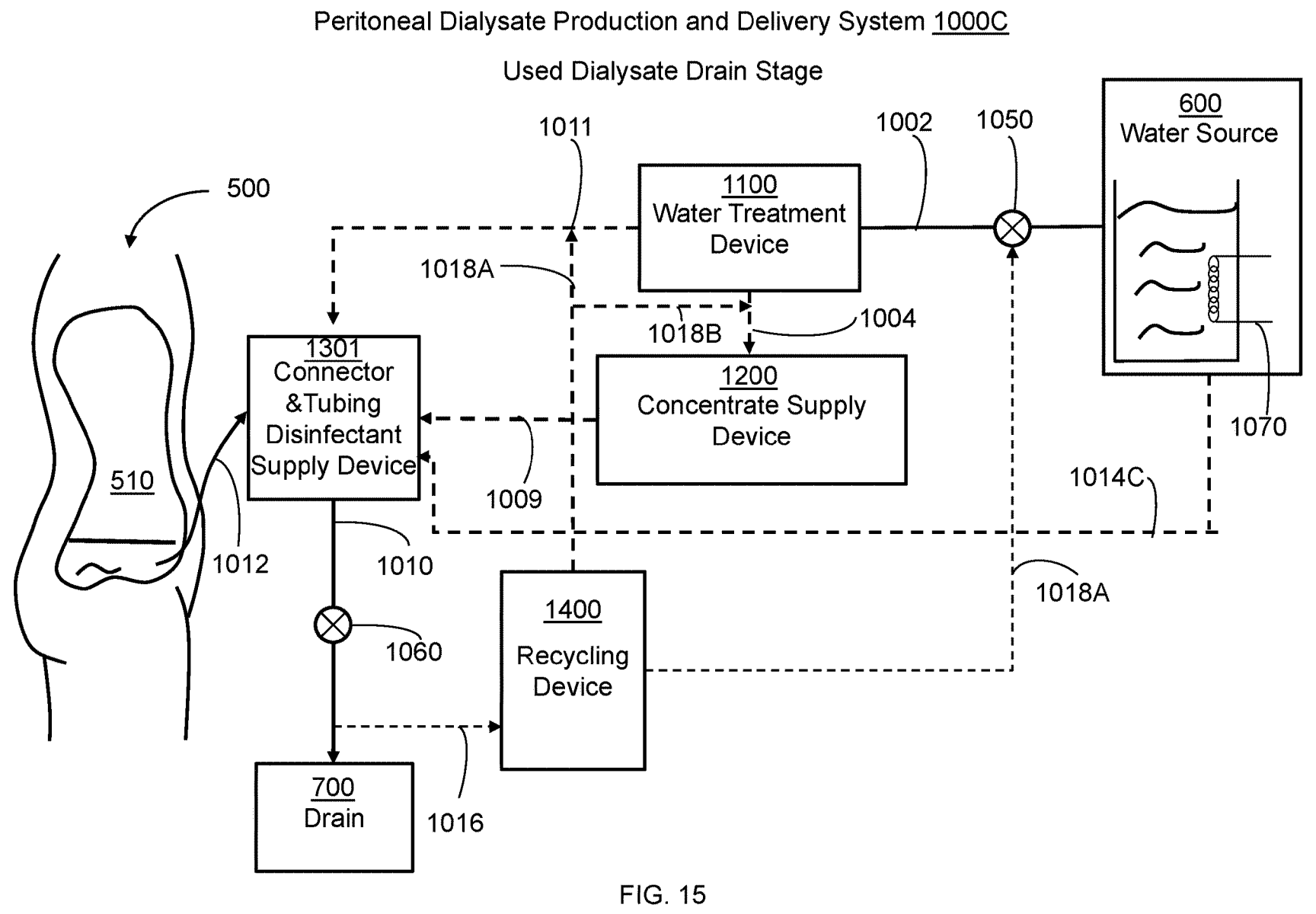

Additional reference is made to FIG. 15. A used dialysate drain stage may be employed to drain used dialysate from peritoneal cavity 510. Analogous to what has been described with respect to PD system 1000A, used peritoneal dialysate may be drained from peritoneal cavity 510 via patient catheter 1012, connector & tubing disinfectant supply device 1301 and waste tubing 1010 to drain 700.

Further referring to FIG. 16, a used water recycling stage may be employed instead of or in addition to the used dialysate drain stage.

In some embodiments, all of used dialysate may be recycled by recycling device 1400.

In some embodiments, a portion of the used dialysate may be drained, e.g., to flush out a certain amount of waste, and another portion may be recycled by recycling device 1400.

The amount of used dialysate may be controlled for example, via a controllable shunt valve (not shown) and based on sensor output provided by sensors (not shown) measuring various characteristics of the used dialysate water.

Figure 17:
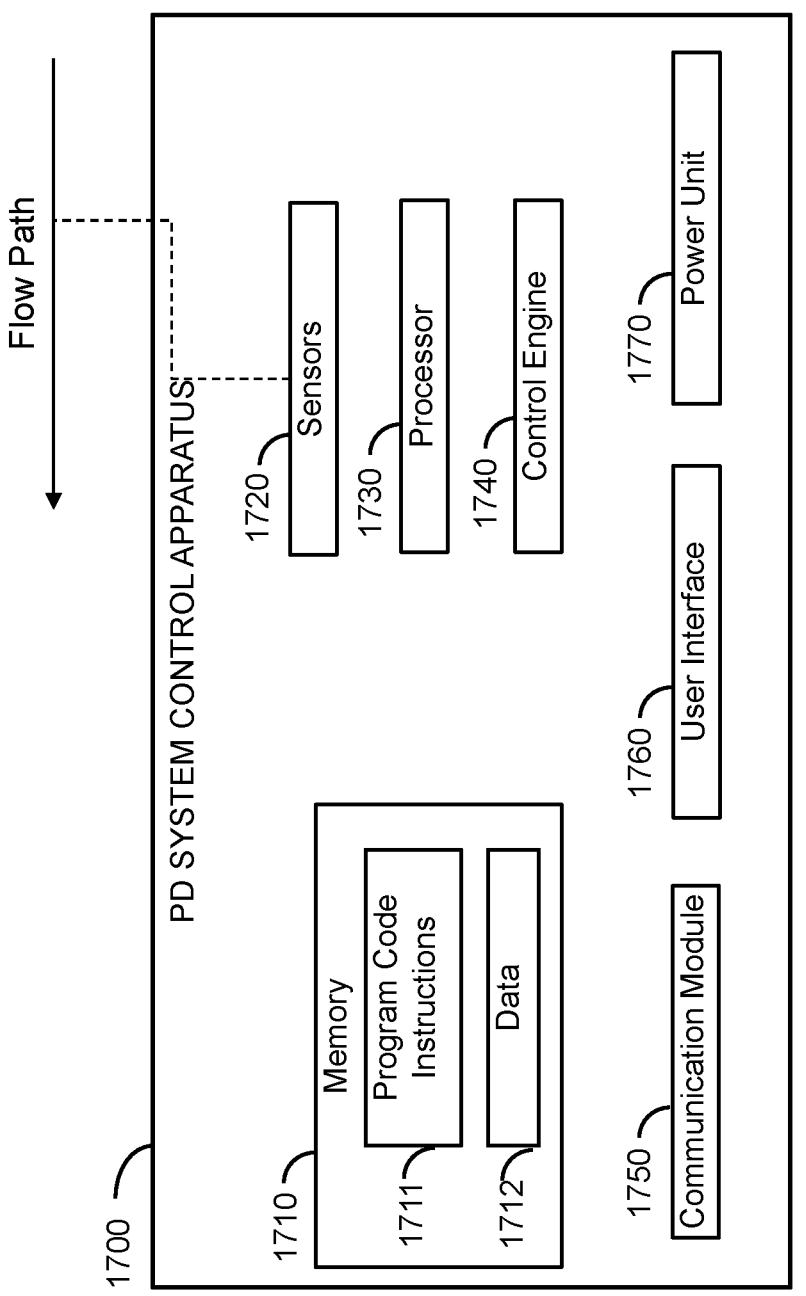
FIG. 17 is a schematic illustration of a PD system control apparatus, according to some embodiments.

Additional reference is made to FIG. 17. In some embodiments, a PD system control apparatus 1700 may comprise a memory 1710 which may store software such as program code instructions 1711 and/or data 1712; sensors 1720 which may be configured to sense physical quantities relating for example to fluid (e.g., water, fresh and/or used dialysate) flowing in the PD system; and/or PD system operating parameters. Sensors 1720 may be operable to generate electronic signals responsive to sensing of the physical quantities.

PD system control apparatus 1700 may further comprise a processor 1730 operable to process the electronic signals generated by the sensors to generate data descriptive of the signals for storage in memory 1710. Processor 1730 may further be configured to process data 1712 stored in memory 1710, for example, by executing program code instructions 1711 to result in a control engine to implement a method a disclosed herein. Data 1712 may for example be processed to analyze the signals and/or for controlling operation of PD system components to result in a control engine 1740.

A communication module 1750 may be employed, for example, to provide an output related to the processing of data stored in memory 1710. Such output may for example be provided to a user interface 1760.

A power unit 1770 may be employed for powering the various components of PD system including, for example, the components of PD system control unit.

The components of PD system control apparatus 1700 may be communicably coupled with each other via wired and/or wireless communication links.

In some embodiments, the PD systems may be operable to perform self-calibration of PD system operating parameters such as, for example, water temperature, flow rate, amount of osmotic agent supply, etc.

Memory 1710 may be in some embodiments storing system information including, for example, product type, product catalog number, chemical content, manufacturing date, manufacturing lot, manufacturing location, expiration date(s), etc. Optionally, the system information may be provided to the user, e.g., via a computerized device like, e.g., a computerized mobile device such as a smartphone.

In some embodiments, the various stages and/or processes described herein may be performed automatically. For example, a disinfection stage may be initiated automatically by PD system control apparatus.

In some embodiments, the various stages and/or processes described herein may be performed "passively" and/or semi-automatically. For example, a disinfection stage may occur when water comes into contact with the disinfecting agent. In some embodiments, stages and/or processes described herein may be initiated automatically by the PD system control apparatus.

In some embodiments, the PD system control apparatus may provide an output indicative of a stage to be employed. For example, the PD system control apparatus may comprise an infection sensor that is operable to sense characteristics related to dialysate waste. Depending on the sensed characteristics, the PD system control apparatus may provide an output indicating that a disinfection stage, and/or a fresh dialysate delivery stage is to be employed.

In some embodiments, the various stages and/or processes described herein may be initiated manually.

Additional reference is now made to FIGS. 18-F. As shown in FIG. 18A, according to some embodiments, a method for performing peritoneal dialysis may comprise executing a tubing disinfection stage (block 1802), performing a fresh dialysate delivery stage (block 1804), and then executing a used dialysate drain and/or recycling stage (block 1806). The sequence of stages outlined with respect to blocks 1802-1806 may be repeated a plurality of times.

As shown in FIG. 18B, according to some embodiments, a method for performing peritoneal dialysis may comprise executing a fresh dialysate delivery stage (block 1822), executing a tubing disinfection stage (block 1824), and then executing a used dialysate drain stage (block 1826). The sequence of stages outlined with respect to blocks 1822-1826 may be repeated a plurality of times.

As shown in FIG. 18C, according to some embodiments, a method for performing peritoneal dialysis may comprise executing a fresh dialysate delivery stage (block 1832), then executing a used dialysate drain and/or recycling stage (block 1834), and then executing a tubing disinfection stage (block 1836). The sequence of stages outlined with respect to blocks 1832-1836 may be repeated a plurality of times.

As shown in FIG. 18D, according to some embodiments, a method for performing peritoneal dialysis may comprise executing a tubing disinfection stage (block 1842), executing a used dialysate drain and/or recycling stage (block 1844) and executing a fresh dialysate delivery stage (block 1846). The sequence of stages outlined with respect to blocks 1842-1846 may be repeated a plurality of times.

As shown in FIG. 18E, according to some embodiments, a method for performing peritoneal dialysis may comprise executing a used dialysate drain and/or recycling stage (block 1852), executing a tubing disinfection stage (block 1854), and executing a fresh dialysate drain stage (block 1856). The sequence of stages outlined with respect to blocks 1852-1876 may be repeated a plurality of times.

As shown in FIG. 18F, according to some embodiments, a method for performing peritoneal dialysis may comprise executing a used dialysate drain stage (block 1862), executing a fresh dialysate delivery stage (block 1864), and executing a tubing disinfection stage (block 1866). The sequence of stages outlined with respect to blocks 1862-1866 may be repeated a plurality of times.

Any suitable combination of sequence of stages outlined herein may be employed.

Figure 19:
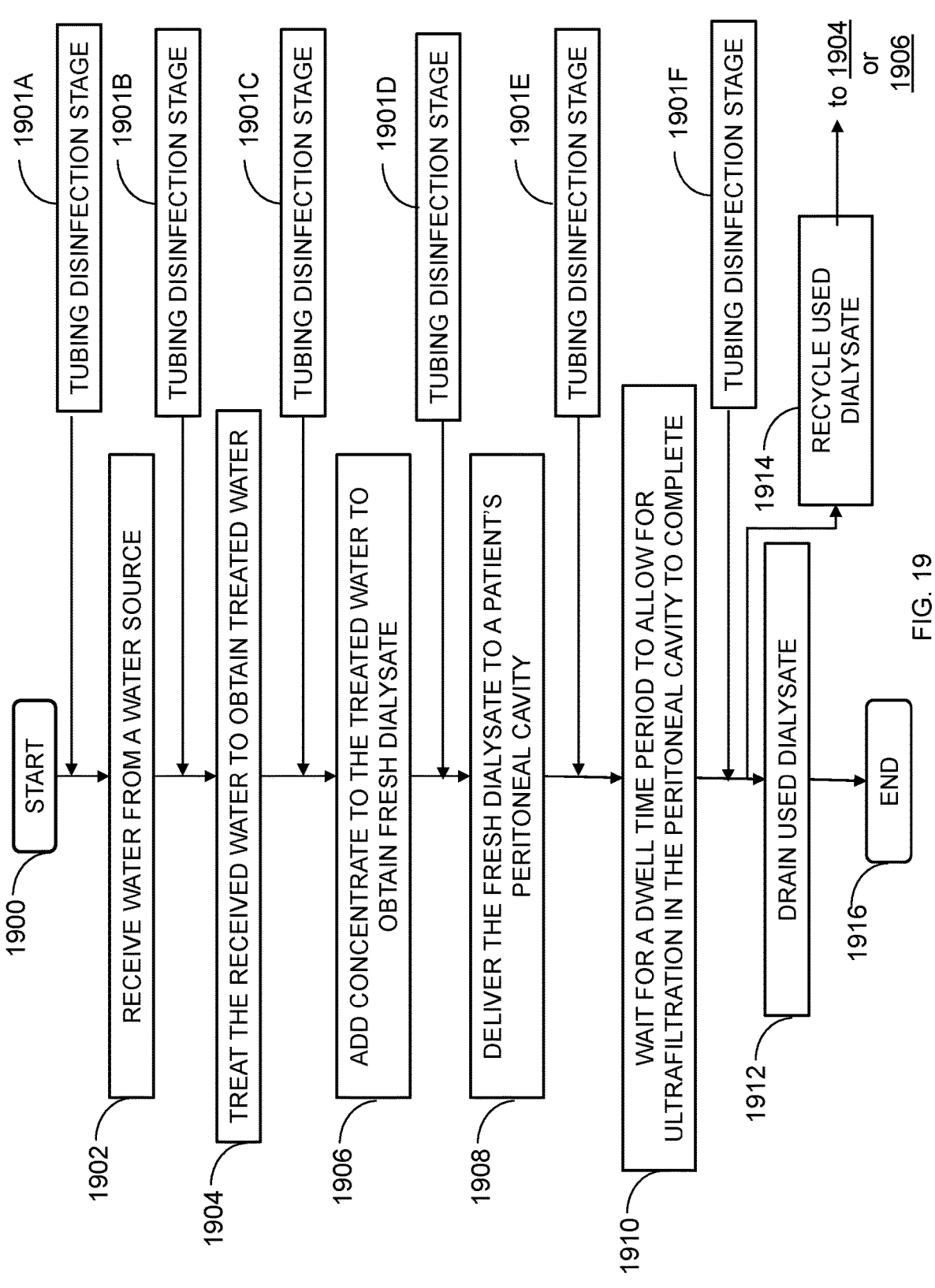
FIG. 19 is a flow chart of a method for performing fresh dialysate production and delivery, the flow chart exemplifying when a disinfection stage can be employed during fresh dialysate production and delivery, according to some embodiments.

Additional reference is made to FIG. 19. According to some embodiments, a disinfection stage (block 1901) can be performed at various points of a fresh dialysate production and delivery stage.

For example, a tubing disinfection stage (block 1901A) may be performed right after start (block 1900) prior to receiving water from a water source (block 1902), for example, at a water treatment device 1100.

In a further example, the tubing disinfection stage (block 1901B) may be performed after receiving water from a water source (block 1902) yet prior to treating the received water to obtain treated water (block 1904).

In an additional example, the tubing disinfection stage (block 1901C) may be performed after treating the received water (block 1904) but before adding concentrate to the treated water to obtain fresh dialysate (block 1906).

In a further example, the tubing disinfection stage (block 1901D) may be performed after adding concentrate to the treated water (block 1906) but before delivering the fresh dialysate to a patient's peritoneal cavity (block 1908).

In another example, the tubing disinfection stage (block 1901E) may be performed after delivery of the fresh dialysate to a patient's peritoneal cavity, yet just at the beginning or during a dwell time period to allow for ultra-filtration in the peritoneal cavity to complete (block 1910).

In a further example, the tubing disinfection stage (block 1901F) may be performed prior to the passing of the dwell time period (block 1910) but before drainage of the used dialysate (block 1912).

Optionally, the tubing disinfection stage may be performed after drainage of used dialysate (block 1912).

Clearly, the tubing disinfection stage may be executed a plurality of times, for example, at each station or point in time of a peritoneal dialysis cycle, e.g., as outlined herein with respect to FIG. 19, prior to completion of the one or more stages (block 1916).

In some embodiments, instead of draining, used dialysate may be recycled, e.g., by recycling device 1400 (block 1914).

In some embodiments, used dialysate may be drained after having performed several recycling processes for the production of fresh dialysate.

In some embodiments, the tubing disinfection may include disinfection of upstream piping 1016 leading towards recycling device 1400, of piping 1018 extending from recycling device 1400 in direction of water treatment device 1100 and/or of recycling device 1400 itself.

In some embodiments, tubing disinfection may be performed concurrently with the supply of water to a treatment device.

In some embodiments, tubing disinfection may be performed concurrently with the treatment of water by a treatment device.

In some embodiments, tubing disinfection may be performed while adding concentration to treated water to obtain a fresh dialysate.

In some embodiments, tubing disinfection may be performed during delivery of fresh dialysate to a peritoneal cavity.

In some embodiments, tubing disinfection may be performed during a dwell time period of an ultrafiltration process.

In some embodiments, tubing disinfection may be performed during drainage of used dialysate.

Additional examples:

Examples 1 pertains to a peritoneal dialysate production and delivery (PD) system for producing fresh dialysate for use in peritoneal dialysis of a patient, the system comprising: a water inlet; a water treatment device that is fluidly connectable or connected via the water inlet to a water source and configured to treat water received from the water source to generate treated water; a concentrate supply device that is in fluid communication with the at least one water treatment device to add concentrate comprised in the concentrate supply device to the treated water to generate fresh dialysate fluid; tubing having a lumen for supplying the fresh dialysate fluid to a patient body via a flow path; and a tubing disinfectant supply device that contains and/or that is operable to receive disinfectant agents, wherein the tubing disinfectant supply device is in fluid connection with the tubing for disinfecting at least a portion of the tubing.

Example 2 includes the subject matter of Example 1 and, optionally, wherein the tubing comprises: a patient catheter having a proximal end for positioning inside the patient body and a distal end; a disinfectant supply tubing; a fresh dialysate supply tubing; a dialysate waste tubing; and a tubing connector for fluidly connecting the fresh dialysate supply tubing portion and the waste dialysate waste tubing with the distal end of the patient catheter.

Example 3 includes the subject matter of Example 2 and, optionally, wherein the disinfectant supply tubing is part of the fresh dialysate supply tubing.

Example 4 includes the subject matter of Example 3 and, optionally, wherein the tubing disinfectant supply tubing is separate from the fresh dialysate supply tubing.

Example 5 includes the subject matter of Example 3 and, optionally, wherein the tubing disinfectant supply tubing and the fresh dialysate supply tubing are fluidly coupled, in parallel, with the tubing connector.

Example 6 includes the subject matter of any one or more of the Examples 1 to 5 and, optionally, wherein the water treatment device comprises any one or more of the following: a water filter apparatus; a water disinfection apparatus for generating disinfected water; and a water conditioning apparatus for generating preconditioned water.

Example 7 includes the subject matter of any one or more of the Examples 1 to 6 and, optionally, a supply pump device for expending energy onto water for forcing water received by the PD system via the tubing, through the water treatment device and the concentrate supply device for providing the patient with fresh dialysate.

Example 8 includes the subject matter of any one or more of the Examples 1 to 7 and, optionally, wherein the tubing connector comprises a manifold for operably connecting the patient catheter with the disinfectant supply tubing, the fresh dialysate supply tubing, and the waste dialysate waste tubing with each other.

Example 9 includes the subject matter of any one or more of the Examples 1 to 8 and, optionally, wherein the manifold is configured to selectively fluidly connect the patient catheter with and disconnect the patient catheter from one or more of the following: the disinfectant supply tubing, the fresh dialysate supply tubing, and the waste dialysate waste tubing.

Example 10 includes the subject matter of Example 8 or Example 9 and, optionally, wherein the manifold comprises manifold valves and tubing for selectively fluidly connecting the patient catheter with and disconnecting the patient catheter from one or more of the following: the disinfectant supply tubing, the fresh dialysate supply tubing, and the waste dialysate waste tubing.

Example 11 includes the subject matter of any one or more of the Examples 1 to 10 and, optionally, wherein the tubing disinfecting agent is approved for use inside a human body.

Example 12 includes the subject matter of any one or more of the Examples 1 to 11 and, optionally, wherein the tubing disinfecting agent is biocompatible and, optionally, biodegradable.

Example 13 includes the subject matter of any one or more of the Examples 1 to 12 and, optionally, wherein the concentrate comprises an osmotic agent.

Example 14 includes the subject matter of any one or more of the Examples 1 to 13 and, optionally, wherein a bypass flow path fluidly connects a water source with the tubing disinfectant supply device by bypassing the water treatment device and/or the concentrate supply device.

Example 15 includes the subject matter of any one or more of the Examples 1 to 15 and, optionally, further comprising a recycling device configured to recycle used dialysate to generate recycled feed water.

Example 16 pertains to a method for performing peritoneal dialysis in a patient, comprising: performing disinfecting stage with a disinfecting agent for disinfecting at least part of a tubing employed for producing and/or delivering fresh dialysate to a patient.

Example 17 includes the subject matter of Example 16 and, optionally, wherein a peritoneal dialysate production and delivery (PD) system comprises the disinfection agent in preparation of the disinfecting stage.

Example 18 includes the subject matter of Example 17 and, optionally, wherein the disinfection agent is provided to the PD system at a patient site (e.g., only) prior to initiating the disinfecting stage.

Example 19 includes the subject matter of any one or more of the Examples 16 to 18 and, optionally, wherein the disinfecting stage is performed prior to performing a fresh dialysate delivery stage; after performing a fresh dialysate deliver stage yet before executing a used dialysate drain stage; and/or after performing the used dialysate drain stage.

Example 20 includes the subject matter of any one or more of the Examples 16 to 19 and, optionally, wherein the tubing disinfection stage is performed: prior to receiving water from a water source; after receiving water from the water source but prior to treating the water for obtaining treated water; after treating the water but prior to adding concentrate to the treated water for obtaining fresh dialysate; after adding concentrate to the treated water but prior to delivering the fresh dialysate to a patient's peritoneal cavity; prior to and/or during waiting for a dwell time to allow for ultrafiltration in the peritoneal cavity to complete; after the dwell time has passed but prior to draining and/or recycling the used dialysate; and/or after the draining of used dialysate to drain and/or after recycling the used dialysate to produce recycled feed water.

Example 21 includes the subject matter of any one or more of the Examples 16 to 20 and, optionally, wherein the tubing disinfection stage is performed: prior to receiving water from a water source; after receiving water from the water source but prior to treating the water for obtaining treated water; after treating the water but prior to adding concentrate to the treated water for obtaining fresh dialysate; after adding concentrate to the treated water but prior to delivering the fresh dialysate to a patient's peritoneal cavity; prior to and/or during waiting for a dwell time to allow for ultrafiltration in the peritoneal cavity to complete; after the dwell time has passed but prior to draining used dialysate; and/or after the draining of used dialysate to drain.

It is noted that the expressions "concurrently", "simultaneously", "in real-time", "constant" as used herein may also encompass, respectively, the meaning of the expression "substantially concurrently", "substantially simultaneously", "substantially in real-time" and "substantially constant".

Any digital computer system, module and/or engine exemplified herein can be configured or otherwise programmed to implement a method disclosed herein, and to the extent that the system, module and/or engine is configured to implement such a method, it is within the scope and spirit of the disclosure. Once the system, module and/or engine are programmed to perform particular functions pursuant to computer readable and executable instructions from program software that implements a method disclosed herein, it in effect becomes a special purpose computer particular to embodiments of the method disclosed herein. The methods and/or processes disclosed herein may be implemented as a computer program product that may be tangibly embodied in an information carrier including, for example, in a non-transitory tangible computer-readable and/or non-transitory tangible machine-readable storage device. The computer program product may directly loadable into an internal memory of a digital computer, comprising software code portions for performing the methods and/or processes as disclosed herein.

Additionally or alternatively, the methods and/or processes disclosed herein may be implemented as a computer program that may be intangibly embodied by a computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

These computer readable and executable instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable and executable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

It is important to note that the method may include is not limited to those diagrams or to the corresponding descriptions. For example, the method may include additional or even fewer processes or operations in comparison to what is described in the figures. In addition, embodiments of the method are not necessarily limited to the chronological order as illustrated and described herein.

Discussions herein utilizing terms such as, for example, "processing", "computing", "calculating", "determining", "establishing", "analyzing", "checking", "estimating", "deriving", "selecting", "inferring" or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes. The term determining may, where applicable, also refer to "heuristically determining".

It should be noted that where an embodiment refers to a condition of "above a threshold", this should not be construed as excluding an embodiment referring to a condition of "equal or above a threshold". Analogously, where an embodiment refers to a condition "below a threshold", this should not to be construed as excluding an embodiment referring to a condition "equal or below a threshold". It is clear that should a condition be interpreted as being fulfilled if the value of a given parameter is above a threshold, then the same condition is considered as not being fulfilled if the value of the given parameter is equal or below the given threshold. Conversely, should a condition be interpreted as being fulfilled if the value of a given parameter is equal or above a threshold, then the same condition is considered as not being fulfilled if the value of the given parameter is below (and only below) the given threshold.

It should be understood that where the claims or specification refer to "a" or "an" element and/or feature, such reference is not to be construed as there being only one of that element. Hence, reference to "an element" or "at least one element" for instance may also encompass "one or more elements".

Terms used in the singular shall also include the plural, except where expressly otherwise stated or where the context otherwise requires.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Unless otherwise stated, the use of the expression "and/or" between the last two members of a list of options for selection indicates that a selection of one or more of the listed options is appropriate and may be made, and may be used interchangeably with the expressions "at least one of the following", "any one of the following" or "one or more of the following", followed by the list of options.

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, examples and/or optional implementation are not to be considered essential features of those embodiments, unless the embodiment, example and/or optional implementation is inoperative without those elements.

The number of elements shown in the Figures should by no means be construed as limiting and is for illustrative purposes only.

As used herein, if a machine (e.g., a processor) is described as "configured to" or "operable to" perform a task (e.g., configured to cause application of a predetermined field pattern), then, at least in some embodiments, the machine may include components, parts, or aspects (e.g., software) that enable the machine to perform a particular task. In some embodiments, the machine may perform this task during operation. Similarly, when a task is described as being done "in order to" establish a target result (e.g., in order to apply a plurality of electromagnetic field patterns to the object), then, at least in some embodiments, carrying out the task may accomplish the target result.

Throughout this application, various embodiments may be presented in and/or relate to a range format. It should be understood that the description in range format is merely for convenience and brevity and should not be construed as an inflexible limitation on the scope of the embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Where applicable, whenever a numerical range is indicated herein, it is meant to include any cited numeral (fractional or integral) within the indicated range.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

Unless otherwise specified, the terms 'about' and/or 'close' with respect to a magnitude or a numerical value may imply to be within an inclusive range of −10% to +10% of the respective magnitude or value.

While the invention has been described with respect to a limited number of embodiments, these should not be construed as limitations on the scope of the invention, but rather as exemplifications of some of the embodiments.

What is claimed is:

1. A portable peritoneal dialysate production and delivery (PD) system for producing fresh dialysate for use in peritoneal dialysis of a patient, the portable system comprising:
   a water treatment device fluidly connectable or connected via a water inlet to a water source and configured to treat water received from the water source to generate treated water;
   a concentrate supply device in fluid communication with at least one of water treatment devices and configured to add concentrate contained in the concentrate supply device to the treated water to generate fresh dialysate fluid;
   a tubing having a lumen for supplying the fresh dialysate fluid to a patient body via a flow path;
   a tubing disinfectant supply device configured to contain and/or receive disinfectant agents, wherein the tubing disinfectant supply device is in fluid connection with the tubing for disinfecting at least a portion of the tubing; and
   a bypass flow path fluidly connecting the water source with the tubing disinfectant supply device by bypassing the water treatment device and/or the concentrate supply device.

2. The portable PD system of claim 1, wherein the tubing comprises:
   a patient catheter having a proximal end for positioning inside the patient body and a distal end;
   a disinfectant supply tubing;
   a fresh dialysate supply tubing;
   a dialysate waste tubing; and a tubing connector for fluidly connecting the fresh dialysate supply tubing and the dialysate waste tubing with the distal end of the patient catheter.

3. The portable PD system of claim 2, wherein the disinfectant supply tubing is part of the fresh dialysate supply tubing.

4. The portable PD system of claim 2, wherein the disinfectant supply tubing is separate from the fresh dialysate supply tubing.

5. The portable PD system of claim 3, wherein the disinfectant supply tubing and the fresh dialysate supply tubing are fluidly coupled, in parallel, with the tubing connector.

6. The portable PD system of claim 1, wherein the water treatment device comprises any one or more of the following:
    a water filter apparatus;
    a water disinfection apparatus for generating disinfected water; and
    a water conditioning apparatus for generating preconditioned water.

7. The portable PD system of claim 1, further comprising:
    a supply pump device for expending energy onto water for forcing water received by the PD system via the tubing, through the water treatment device and the concentrate supply device for providing the patient with fresh dialysate.

8. The portable PD system of claim 2, wherein the tubing connector comprises a manifold for operably connecting the patient catheter with the disinfectant supply tubing, the fresh dialysate supply tubing, and the dialysate waste tubing with each other.

9. The portable PD system of claim 8, wherein the manifold is configured to selectively fluidly connect the patient catheter with and disconnect the patient catheter from one or more of the following: the disinfectant supply tubing, the fresh dialysate supply tubing, and the dialysate waste tubing.

10. The portable PD system of claim 9, wherein the manifold comprises manifold valves and tubing for selectively fluidly connecting the patient catheter with and disconnecting the patient catheter from one or more of the following: the disinfectant supply tubing, the fresh dialysate supply tubing, and the dialysate waste tubing.

11. The portable PD system of claim 1, wherein the disinfecting agent is biocompatible and, optionally, biodegradable.

12. The portable PD system of claim 1, wherein the concentrate supply device comprises fin elements having surface portions extending into a flow path of treated water to generate fresh dialysate fluid.

13. The portable PD system of claim 1, further comprising a recycling device configured to recycle used dialysate to generate recycled feed water.

14. A method for performing peritoneal dialysis in a patient, comprising:

performing a disinfecting stage with a disinfecting agent for disinfecting at least part of a tubing employed for producing and/or delivering a fresh dialysate to a patient, wherein the method employs a portable peritoneal dialysate production and delivery (PD) system comprising:

a water treatment device fluidly connectable or connected via a water inlet to a water source and configured to treat water received from the water source to generate treated water;

a concentrate supply device in fluid communication with at least one of water treatment devices and configured to add concentrate contained in the concentrate supply device to the treated water to generate fresh dialysate fluid;

a tubing having a lumen for supplying the fresh dialysate fluid to a patient body via a flow path;

a tubing disinfectant supply device configured to contain and/or to receive disinfectant agents, wherein the tubing disinfectant supply device is in fluid connection with the tubing for disinfecting at least a portion of the tubing; and a bypass flow path fluidly connecting the water source with the tubing disinfectant supply device by bypassing the water treatment device and/or the concentrate supply device.

15. The method of claim 14, wherein a peritoneal dialysate production and delivery (PD) system comprises the disinfection agent in preparation of the disinfecting stage.

16. The method of 15, wherein the disinfection agent is provided to the PD system at a patient site prior to initiating the disinfecting stage.

17. The method of claim 14, wherein the disinfecting stage is performed prior to performing a fresh dialysate delivery stage; after performing a fresh dialysate deliver stage yet before executing a used dialysate drain and/or used dialysate recycling stage; and/or after performing the used dialysate drain or recycling stage.

18. The method of claim 14, wherein the disinfection stage is performed:
    prior to receiving water from a water source;
    after receiving water from the water source but prior to treating the water for obtaining treated water;
    after treating the water but prior to adding concentrate to the treated water for obtaining the fresh dialysate;
    after adding concentrate to the treated water but prior to delivering the fresh dialysate to a patient's peritoneal cavity;
    prior to and/or during waiting for a dwell time to allow for ultrafiltration in the peritoneal cavity to complete;
    after the dwell time has passed but prior to draining and/or recycling used dialysate; and/or
    after the draining of used dialysate to drain and/or after recycling the used dialysate to produce recycled feed water.

* * * * *